US008475406B2

(12) United States Patent
Bagwell et al.

(10) Patent No.: US 8,475,406 B2
(45) Date of Patent: Jul. 2, 2013

(54) INFLATABLE RETENTION SYSTEM FOR ENTERAL FEEDING DEVICE

(75) Inventors: Alison S. Bagwell, Alpharetta, GA (US); Thomas G. Estes, Bonifay, FL (US); Donald J. McMichael, Roswell, GA (US); John A. Rotella, Roswell, GA (US); Scott M. Teixeira, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/443,991

(22) Filed: Apr. 11, 2012

(65) Prior Publication Data

US 2012/0197192 A1 Aug. 2, 2012

Related U.S. Application Data

(62) Division of application No. 12/977,945, filed on Dec. 23, 2010, now Pat. No. 8,177,742.

(51) Int. Cl.
*A61M 29/00* (2006.01)

(52) U.S. Cl.
USPC .................................................... 604/100.01

(58) Field of Classification Search
USPC .................. 604/96.01, 97.01, 97.03, 100.01, 604/100.02, 100.03
See application file for complete search history.

(56) References Cited

U.S. PATENT DOCUMENTS

| | | | | |
|---|---|---|---|---|
| 3,050,066 A | | 8/1962 | Koehn | |
| 3,725,522 A | | 4/1973 | Sheridan et al. | |
| 3,915,171 A | | 10/1975 | Shermeta | |
| 4,207,900 A | | 6/1980 | Patel et al. | |
| 4,251,305 A | | 2/1981 | Becker et al. | |
| 4,315,513 A | | 2/1982 | Nawash et al. | |
| 4,588,398 A | | 5/1986 | Daugherty et al. | |
| 4,661,095 A | | 4/1987 | Taller et al. | |
| 4,771,777 A | | 9/1988 | Horzewski et al. | |
| 4,874,373 A | | 10/1989 | Luther et al. | |
| 4,944,732 A | | 7/1990 | Russo | |
| 5,053,004 A | | 10/1991 | Markel et al. | |
| 5,074,845 A | | 12/1991 | Miraki et al. | |
| 5,125,897 A | * | 6/1992 | Quinn et al. | 604/99.03 |
| 5,207,648 A | | 5/1993 | Gross | |

(Continued)

FOREIGN PATENT DOCUMENTS

| | | |
|---|---|---|
| DE | 203 02 536 U1 | 5/2003 |
| EP | 0 109 657 A1 | 5/1984 |

(Continued)

*Primary Examiner* — Theodore J Stigell
*Assistant Examiner* — Aarti B Berdichevsky
(74) *Attorney, Agent, or Firm* — Karl V. Sidor

(57) ABSTRACT

An inflatable retention system for an enteral feeding tube having a base deployed outside the human body and an indwelling retainer which is deployed within a lumen or cavity of the body by insertion through a stoma from outside the body. The retention system includes a tube having a proximal end, a distal end, an external tube diameter, and tube walls defining a feeding lumen and an inflation lumen. The retention system also includes an inflatable balloon located at a distal end of the tube in fluid communication with the inflation lumen, the balloon having thin, flexible walls, a predetermined spheroid shape, and a volume at which a fluid in the balloon is under no pressure such that upon inflation with a fluid to pressurize fluid in the balloon, the balloon assumes a stable spheroid shape and exhibits a substantially linear pressure versus volume curve.

10 Claims, 13 Drawing Sheets

U.S. PATENT DOCUMENTS

| | | | |
|---|---|---|---|
| 5,250,029 | A | 10/1993 | Lin et al. |
| 5,308,325 | A | 5/1994 | Quinn et al. |
| 5,439,443 | A | 8/1995 | Miyata et al. |
| 5,484,420 | A | 1/1996 | Russo |
| 5,500,180 | A | 3/1996 | Anderson et al. |
| 5,662,703 | A | 9/1997 | Yurek et al. |
| 5,716,572 | A | 2/1998 | Lesiczka et al. |
| 5,736,085 | A | 4/1998 | Brown et al. |
| 5,964,778 | A | 10/1999 | Fugoso et al. |
| 6,019,746 | A * | 2/2000 | Picha et al. .................. 604/175 |
| 6,077,243 | A * | 6/2000 | Quinn ........................ 604/93.01 |
| 6,206,852 | B1 | 3/2001 | Lee |
| 6,264,633 | B1 | 7/2001 | Knorig |
| 6,344,045 | B1 | 2/2002 | Lim et al. |
| 6,506,179 | B1 | 1/2003 | Tiefenthal et al. |
| 6,506,180 | B1 | 1/2003 | Lary |
| 6,673,302 | B2 | 1/2004 | Wang et al. |
| 6,878,130 | B2 * | 4/2005 | Fournie et al. ........... 604/100.01 |
| 6,946,173 | B2 | 9/2005 | Lim et al. |
| 6,951,674 | B1 | 10/2005 | Wu |
| 7,112,186 | B2 | 9/2006 | Shah |
| 7,534,224 | B2 | 5/2009 | Triebes et al. |
| 8,142,394 | B1 * | 3/2012 | Rotella et al. ............ 604/100.03 |
| 8,177,742 | B1 * | 5/2012 | Bagwell et al. .......... 604/100.01 |
| 8,206,347 | B2 * | 6/2012 | Burnside et al. ......... 604/101.01 |
| 2002/0193753 | A1 | 12/2002 | Rouns et al. |
| 2002/0198491 | A1 | 12/2002 | Miller et al. |
| 2003/0074017 | A1 | 4/2003 | Shah |
| 2003/0225376 | A1 | 12/2003 | Fournie et al. |
| 2003/0225392 | A1 * | 12/2003 | McMichael et al. .......... 604/509 |
| 2004/0006333 | A1 | 1/2004 | Arnold et al. |
| 2004/0034320 | A1 | 2/2004 | Burnett |
| 2004/0106899 | A1 | 6/2004 | McMichael et al. |
| 2004/0106901 | A1 | 6/2004 | Letson et al. |
| 2004/0122464 | A1 | 6/2004 | Wang et al. |
| 2004/0197501 | A1 | 10/2004 | Sridharan |
| 2004/0215141 | A1 | 10/2004 | Clarke et al. |
| 2005/0038381 | A1 * | 2/2005 | McMichael ................ 604/96.01 |
| 2005/0124935 | A1 | 6/2005 | McMichael |
| 2006/0095065 | A1 * | 5/2006 | Tanimura et al. ............. 606/194 |
| 2006/0116658 | A1 * | 6/2006 | McMichael et al. .......... 604/509 |
| 2006/0206137 | A1 | 9/2006 | Gazza |
| 2008/0000482 | A1 | 1/2008 | Maguire et al. |
| 2008/0078403 | A1 | 4/2008 | Clayton |
| 2008/0078404 | A1 | 4/2008 | Martens |
| 2008/0142016 | A1 | 6/2008 | Colburn et al. |
| 2008/0188802 | A1 | 8/2008 | Shah |
| 2008/0215034 | A1 | 9/2008 | Clayton et al. |
| 2008/0236593 | A1 | 10/2008 | Nelson et al. |
| 2009/0254033 | A1 | 10/2009 | Suzuki et al. |
| 2010/0185159 | A1 * | 7/2010 | Bagwell et al. ............... 604/256 |
| 2011/0152762 | A1 | 6/2011 | Hershey et al. |

FOREIGN PATENT DOCUMENTS

| | | | |
|---|---|---|---|
| JP | 10-015055 | A | 1/1998 |
| JP | 10-314297 | A | 12/1998 |
| JP | 2006-055438 | A | 3/2006 |
| WO | WO 00/51660 | A1 | 9/2000 |
| WO | WO 01/34240 | A2 | 5/2001 |
| WO | WO 2008/026121 | A2 | 3/2008 |
| WO | WO 2008/109008 | A1 | 9/2008 |
| WO | WO 2008/121603 | A1 | 10/2008 |
| WO | WO 2009/091990 | A1 | 7/2009 |
| WO | WO 2009/135141 | A1 | 11/2009 |

* cited by examiner

INFLATABLE RETENTION SYSTEM FOR ENTERAL FEEDING DEVICE

The present application is a Divisional of U.S. patent application Ser. No. 12/977,945, filed on Dec. 23, 2010, now U.S. Pat. No. 8,177,742 and claims priority thereto.

FIELD OF THE INVENTION

The present invention relates to improved device for retaining an indwelling catheter or tube. More particularly, the present invention relates to a device for retaining gastrostomy tubes or enteral feeding catheters having a base deployed outside the human body and a retainer which is inserted through a stoma from outside the body for deployment within a lumen of the body.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a tube is placed through the stoma. This surgical opening and/or the procedure to create the opening is common referred to as “gastrostomy”. Feeding solutions can be injected through the tube (i.e., a feeding tube) to provide nutrients directly to the stomach or intestines in a procedure generally known as enteral feeding. A variety of different feeding tubes intended for enteral feeding have been developed over the years. These devices are frequently referred to as “gastrostomy tubes”, “percutaneous gastrostomy catheters”, “PEG tubes”, “enteral feeding tubes” or “enteral feeding catheters”.

To prevent the PEG tube from being pulled out of the stomach/intestinal wall, various types of retainers are used at a distal end of the catheter. Examples of conventional devices with Malecot tips or similar expanding tips are found at, for example, U.S. Pat. No. 3,915,171 for “Gastrostomy Tube” issued to Shermeta; U.S. Pat. No. 4,315,513 for “Gastrostomy and Other Percutaneous Transport Tubes” issued to Nawash et al.; U.S. Pat. No. 4,944,732 for “Gastrostomy Port” issued to Russo; and U.S. Pat. No. 5,484,420 for “Retention Bolsters for Percutaneous Catheters” issued to Russo. Exemplary commercial products include the Passport® Low Profile Gastrostomy Device available from Cook Medical, Inc. of Bloomington, Ind. and the Mini One™ Non-Balloon Button available from Applied Medical Technology, Inc. of Brecksville, Ohio. A shortcoming of these devices relates to the manner of insertion and withdrawal of a tube incorporating these retaining fixtures (e.g., a gastrostomy tube) into a body lumen such as into the stomach.

Feeding tubes that are initially placed during the gastrostomy procedure have non-inflatable bumpers, bolsters, Malecot tips or similar expanding tips made of a resilient material.

These devices are passed through esophagus of a patient and into the stomach or intestinal space. The narrow tube end of the device is pulled through the stoma and the bolster or bumper which is much larger than the stoma is retained in the stomach or intestinal space to prevent the device from falling out. It is generally thought that the non-inflatable bumper or bolster helps the stoma site heal properly and form a desired shape.

If the feeding tube having the non-inflatable retainer needs to be replaced, it is frequently replaced with a feeding tube that employs an inflatable balloon as the retainer. The balloon, typically made of a “soft” or elastomeric medical grade silicone, is attached to the end of the catheter and is deflated for insertion through the stoma and then inflated to hold the enteral feeding assembly in position. While these balloons have many advantages, these balloons generally provide a much lower level of retention or resistance to being pulled out through the stoma. The balloons generally take on a spherical shape when inflated. Physicians frequently overinflate these balloons to attempt to reduce the radius of curvature of the balloon at the stoma site. That is, a spherical balloon having a larger diameter will tend to have a slightly flatter profile along an arc having a fixed distance in comparison to a spherical balloon having a smaller diameter. The silicone readily deforms while inflated in response to pulling force and may form a funnel or cone shape that helps it travel through the stoma. Elastomeric or “soft” medical grade silicone has a tendency to “creep” or stress relax over time which can change the dimensions of the balloon. In addition, the thickness of these balloons can make it more difficult to insert and remove an uninflated balloon through the stoma. For example, the thickness of a wall of such a silicone balloon typically ranges from about 300 to over 500 micrometers per wall so that the balloon will increase the diameter of the tube to which it is attached by 600 micrometer to over 1000 micrometers (over 1 millimeter).

One attempt to provide a silicone balloon having a non-spherical shape is described in U.S. Patent Application Publication No. 2004/0106899 published Jun. 3, 2004 for a “Gastric Balloon Catheter with Improved Balloon Orientation”. This publication describes a silicone balloon that is molded, pre-shaped or preformed using non-uniformly thick material or expansion limiters so that upon inflation, the silicone expands radially in a non-uniform manner. However, such devices have unsatisfactory thickness in the region of the balloon that makes it difficult to insert the device through a stoma.

Relatively large changes in pressure are needed to stretch such elastic materials from an unstretched state to expand the balloon. Moreover, the relationship between the amount of pressure needed to stretch such elastic materials to expand the balloon and the volume of the balloon is nonlinear. That is, the correlation between the pressure of the fluid inside the balloon and the volume of the balloon is not simple. For example, FIG. 1A is an illustration of a conventional enteral feeding tube device 10 having a base 12 and retainer balloon 13 made of conventional “soft” or elastomeric medical grade silicone in an un-stretched state (i.e., un-inflated condition). FIG. 1B is an illustration of a conventional enteral feeding tube device 10 having a base 12 and retainer balloon 13 made of conventional “soft” or elastomeric medical grade silicone which has been stretched by inflation to an inflated volume. FIG. 1C is an illustration showing an exemplary relationship between the pressure of a fluid inside such an elastic retainer balloon and the balloon volume during the stretching the conventional “soft” or elastomeric medical grade silicone forming the balloon by increasing the pressure of a fluid inside the balloon. The illustration is a pressure versus volume plot for a Kimberly-Clark® MIC-KEY® 12 French low profile gastrostomy feeding tube with a conventional silicone balloon. As can be seen in FIG. 1C, stretching such elastic balloons from negligible volume (i.e., a deflated condition) at negligible pressure to a deployed volume between about 3 to about 5 milliliters requires an initially large and continuous change in pressure to overcome the resistance to stretching. In this example, an immediate pressure change from zero or negligible pressure to between about 4 to 7 pounds per square inch (28 to 48 kilopascals) is needed to overcome the resistance to stretching needed to inflate such exemplary conventional retainer balloons to a volume of even 1 cubic centimeter (approximately 1 milliliter) and a pressure between about 5 to 10 pounds per square inch (34 to 69 kilopascals) to inflate such conventional "soft" or elastomeric medical grade silicone balloons to a volume of about 3 cubic centimeters (~3 milliliters) with sterile water—although saline solution or air can be used.

Accordingly, there is a need for an improved inflatable retention system for an enteral feeding tube having a base deployed outside the human body and an indwelling retainer which is deployed within a lumen of the body by insertion through a stoma from outside the body. A need exists for a retention system utilizing a balloon that has a collapsed, non-inflated state such that the feeding tube and the thin, flexible walls of the balloon can pass through an orifice that is about the same size as the external diameter of the feeding tube. There is also a need for an inflatable retention system that works well and has a stable shape at relatively low pressures (e.g., 4 pounds per square inch (28 kilopascals) or less). There is also a need for an inflatable retention system that provides a level of retention or resistance to being pulled through a stoma that is equal to or better than non-inflatable retention systems. There is also a need for an enteral feeding tube assembly that incorporates such an inflatable retention system.

SUMMARY OF THE INVENTION

In response to the difficulties and problems discussed herein, the present invention provides an inflatable retention system for an enteral feeding tube having a base deployed outside the human body and an indwelling retainer which is deployed within a cavity or lumen of the body by insertion through a stoma from outside the body. The retention system includes a tube having a proximal end, a distal end, an external tube diameter, and tube walls defining a feeding lumen and an inflation lumen. The system also includes an inflatable balloon located at a distal end of the tube in fluid communication with the inflation lumen. The balloon has thin, flexible walls, a predetermined spheroid shape and a volume at which a fluid in the balloon is under no pressure such that upon inflation with a fluid to pressurize fluid in the balloon, the balloon assumes a stable spheroid shape and exhibits a substantially linear pressure versus volume curve. In an aspect of the invention, the balloon may have a predetermined fill volume as well as a reserve volume; the reserve volume is a volume less than the predetermined fill volume and at which a fluid in the balloon under no pressure—and always more an 0.5 milliliters. The predetermined fill volume is desirably from about 1.01 to about 1.5 times greater than an upper limit of the reserve volume. The balloon desirably has an oblate spheroid shape when inflated beyond the reserve volume. In an aspect of the invention, the ratio of the diameter of the balloon along its minor axis to the diameter of the balloon along its major axis may be from about 0.45 to about 0.65. That is, the diameter of the balloon in the axial dimension that is parallel to the feeding tube to which the balloon is attached in comparison to the diameter of the balloon in the dimension that is perpendicular to the feeding tube may be from about 0.45 to about 0.65. More desirably, the ratio may be from about 0.5 to about 0.6.

The balloon desirably has a collapsed, non-inflated state such that the tube and the thin, flexible walls of the balloon can pass through an orifice having a diameter not more than about 20 percent greater than the external diameter of the tube. In an aspect of the invention, the wall of the balloon has a thickness of from about 5 micrometers to about 100 micrometers. The predetermined fill volume of the balloon desirably corresponds to a fluid pressure in the balloon between 2 to about 9 pounds per square inch (14 to 64 kilopascals). The retention system is particularly advantageous for balloons having a predetermined fill volume at relatively low pressures (e.g., 4 pounds per square inch (28 kilopascals) or less). In another aspect of the invention, the predetermined fill volume may be from about 2 milliliters to about 6 milliliters.

According to the invention, when the balloon is inflated with a fluid beyond the reserve volume to pressurize fluid in the balloon, the material of the balloon assumes a stable spheroid shape and exhibits a substantially linear pressure versus volume curve to at least the predetermined fill volume.

The tube may have an external tube diameter of from about 3 mm to about 9 mm and the balloon may have a diameter of from about 15 mm to about 30 mm at a major axis of the spheroid when inflated to the predetermined fill volume. The ratio of the balloon diameter to the external tube diameter is desirably greater than three. For example, the ratio of the balloon diameter to the external tube diameter is desirably greater than about 3.5. As another example, the ratio of the balloon diameter to the external tube diameter is desirably greater than about 4. As yet another example, the ratio of the balloon diameter to the external tube diameter is desirably greater than about 4.5. As another example, the ratio of the balloon diameter to the external tube diameter is desirably greater than about 5. The tube is desirably formed of a material that is less elastic than conventional silicone tubing used for enteral feeding tubes. As an example, the tube may be formed of a material requiring a tensile force or load of 300 pounds per square inch (psi) at an elongation about 100 percent. As another example, the tube may be formed of a material requiring a tensile force of 500 psi at an elongation about 200 percent.

According to the invention, the retention system may further include a base located at the proximal end of the tube. The base is configured to define an opening to the catheter lumen. The base may have a first end and a second end. An inflation valve may be located on the base. The inflation valve is in fluid communication with the balloon through the inflation lumen in the tube. The base also includes an indicator. The indicator is located on the base in fluid communication with the balloon and the indicator is configured to provide a discrete visual signal that the volume of the balloon is different from a predetermined fill volume or from a reserve volume. In an aspect of the invention, the indicator may provide only a first discrete visual signal when the balloon is inflated to its predetermined fill volume and a second discrete visual signal when the fluid in the balloon is no longer under pressure, with no signal of other inflation states therebetween, whereby the second discrete visual signal provides warning that the balloon volume has reached the reserve volume.

The present invention also encompasses an enteral feeding tube assembly having a base deployed outside the human body and an indwelling retainer which is deployed within a lumen of the body by insertion through a stoma from outside the body. The enteral feeding tube assembly includes a tube having a proximal end, a distal end, an external tube diameter, and tube walls defining a feeding lumen and an inflation lumen. A base is located at the proximal end of the tube and is configured to define an opening to the catheter lumen. The base may have a first end and a second end. An inflation valve is located on the base and is in fluid communication with the balloon through the inflation lumen in the tube.

The assembly also includes an inflatable balloon located at a distal end of the tube in fluid communication with the inflation lumen. The balloon has thin, flexible walls, a predetermined spheroid shape, a predetermined fill volume, and a reserve volume that is less than the predetermined fill volume and at which a fluid in the balloon is under no pressure. The predetermined fill volume may be from about 1.01 to about 1.5 times greater than an upper limit of the reserve volume. The balloon desirably has an oblate spheroid shape when inflated beyond the reserve volume. The balloon desirably has a collapsed, non-inflated state such that the tube and the thin, flexible walls of the balloon can pass through an orifice that is not much greater than the external diameter of the tube. For example, for tubes having a French size ranging from 10 to 14 (e.g., external diameters ranging from about 3.3 mm to about 4.6 mm), the balloon desirably has a collapsed, non-inflated state such that the tube and the thin, flexible walls of the balloon can pass through an orifice that is not more than about 20 percent greater than the external diameter of the tube. For tubes having a French size ranging from 16 to 24 (e.g., external diameters ranging from about 5.3 mm to about 8.0 mm), the balloon desirably has a collapsed, non-inflated state such that the tube and the thin, flexible walls of the balloon can pass through an orifice that is not more than about 10 percent greater than the external diameter of the tube.

The wall of the balloon may have a thickness of from about 5 micrometers to about 100 micrometers. The predetermined fill volume of the balloon desirably corresponds to a fluid pressure in the balloon between 2 to about 9 pounds per square inch (14 to 64 kilopascals). In an aspect of the invention, the predetermined fill volume may be from about 2 milliliters to about 6 milliliters. According to the invention, when the balloon is inflated with a fluid beyond the reserve volume to pressurize fluid in the balloon, the material of the balloon assumes a stable spheroid shape and exhibits a substantially linear pressure versus volume curve to at least the predetermined fill volume.

The base also includes an indicator. The indicator is located on the base in fluid communication with the balloon and the indicator is configured to provide a discrete visual signal that the volume of the balloon is different from a predetermined fill volume or from a reserve volume. In an aspect of the invention, the indicator may provide only a first discrete visual signal when the balloon is inflated to its predetermined fill volume and a second discrete visual signal when the fluid in the balloon is no longer under pressure, with no signal of other inflation states therebetween, whereby the second discrete visual signal provides warning that the balloon volume has reached the reserve volume.

The tube may have an external tube diameter of from about 3 mm to about 9 mm and the balloon may have a diameter of from about 15 mm to about 30 mm at a major axis of the spheroid when inflated to the predetermined fill volume. The ratio of this balloon diameter to the external tube diameter is desirably greater than three. For example, the ratio of this balloon diameter to the external tube diameter is desirably greater than about 3.5. As another example, the ratio of this balloon diameter to the external tube diameter is desirably greater than about 4. As yet another example, the ratio of this balloon diameter to the external tube diameter is desirably greater than about 4.5. The tube is desirably formed of a material that is less elastic than conventional silicone tubing used for enteral feeding tubes. As an example, the tube may be formed of a material requiring a tensile force of 300 psi at an elongation about 100 percent. As another example, the tube may be formed of a material requiring a tensile force of 500 psi at an elongation about 200 percent.

A better understanding of the above and many other features and advantages of the new inflatable retention system for an enteral feeding tube and for the new enteral feeding tube assembly incorporating such an inflatable retention system may be obtained from a consideration of the detailed description of the invention below, particularly if such consideration is made in conjunction with the appended drawings.

DEFINITIONS

As used herein the following terms have the specified meanings, unless the context demands a different meaning or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the phrase "fluid communication" means an unobstructed transmission or passage between two points and/or two structures for a specific purpose. In this example, fluid communication would be a passage which permits liquids and/or gasses to pass.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the terms "align," "aligned," and/or "alignment" refers to the spatial property possessed by an arrangement or position of things in a straight line.

As used herein, the terms "orientation" or "position" used interchangeably herein refer to the spatial property of a place where something is situated or a way in which something is situated; for example, "the position of the hands on the clock."

As used herein, the term "about" adjacent to a stated number refers to an amount that is plus or minus ten (10) percent of the stated number.

As used herein, the term "non-distended" when used with respect to an inflatable balloon joined or mounted to a feeding tube according to the present invention refers to an inflatable balloon which has no radial pressure applied to the balloon's inner surface that is greater than atmospheric pressure or the pressure of the environment immediately surrounding the exterior of the balloon. Non-distended inflatable balloons include, for example, an inflatable balloon mounted on a feeding tube which does not contain a fluid, or which contains a fluid that is not under pressure or a pressure that is less than or equal to atmospheric pressure or the pressure of the environment immediately surrounding the exterior of the balloon. In contrast, the term "distended" when used with respect to an inflatable balloon joined or mounted to a feeding tube according to the present invention refers to an inflatable balloon which is being subjected to pressure applied to the balloon's inner surface that is greater than atmospheric pressure or the pressure of the environment immediately surrounding the exterior of the balloon, such as pressure exerted by a fluid (e.g., pressurized liquid or gas) contained within the balloon.

As used herein, the term "predetermined fill volume" when used with respect to an inflatable balloon joined or mounted to a feeding tube according to the present invention refers to a volume in a range with a lower limit at the transition from a non-distended state to a distended state where the fluid in the balloon is first under pressure and a upper limit that is no more than about 1.5 times (i.e., about fifty percent (50%) greater than) the volume of the balloon at the transition from a non-distended state to a distended state. For example, a predetermined fill volume can be the volume of the balloon at the transition from a non-distended state to a distended state and may encompass a volume of up to about 1.4 times (i.e., about forty percent (40%) greater than) the volume of the balloon at the transition from a non-distended state to a distended state. As another example, a predetermined fill volume can be the volume of the balloon at the transition from a non-distended state to a distended state to a volume up to about 1.2 times (i.e., about twenty percent (20%) greater than) the volume of the balloon at the transition from a non-distended state to a distended state. Conventional elastic balloons which continually distend with increasing pressure are considered to not have a predetermined fill volume. While it might be possible to characterize some elastic balloons as having a transition from a non-distended state to a distended state, such a transition occurs only during the earliest introduction of pressure to initiate stretching or continuous distension of the material of the balloon.

These terms may be defined with additional language in the remaining portions of the specification.

DETAILED DESCRIPTION OF THE INVENTION

Figure 1B:
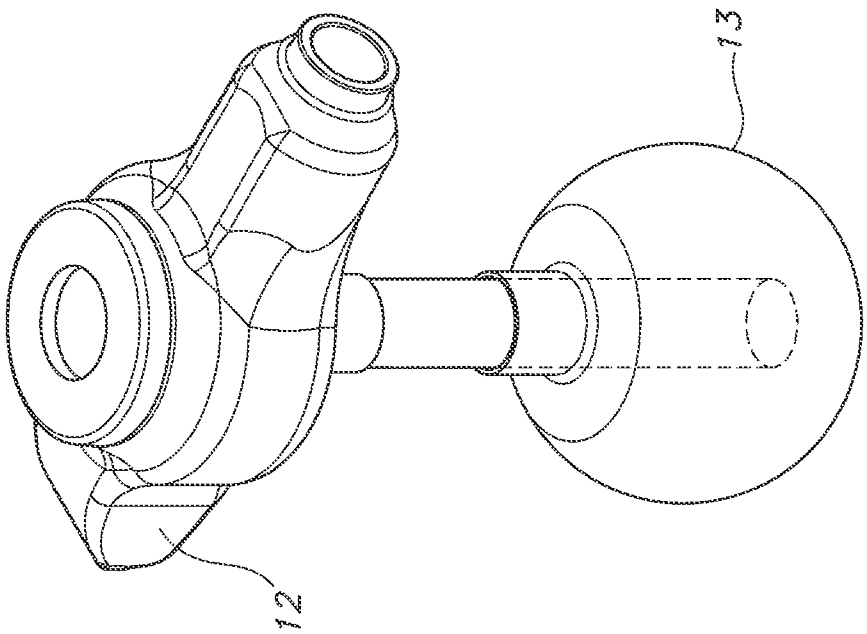
FIG. 1B (PRIOR ART)
FIG. 1B is a perspective view of an exemplary prior art device.
Figure 1A:
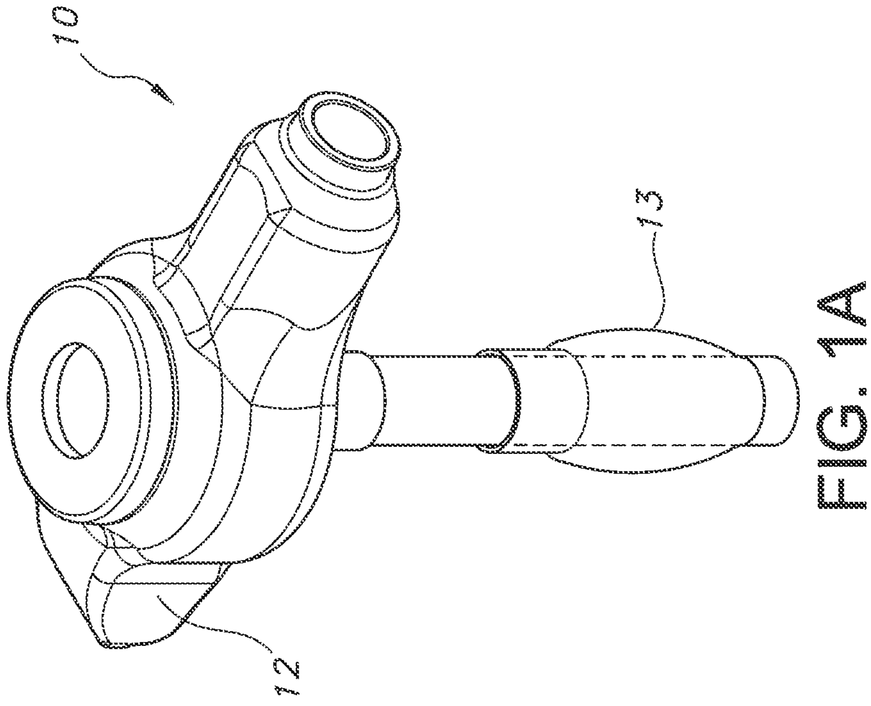
FIG. 1A (PRIOR ART)
FIG. 1A is a perspective view of an exemplary prior art device.

The invention(s) disclosed herein relate generally to improved medical care for patients who require enteral feeding. More particularly, the invention(s) disclosed herein relate to an inflatable retention system for an enteral feeding tube having a base deployed outside the human body and an indwelling retainer which is deployed within a lumen of the body by insertion through a stoma from outside the body.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 2B:
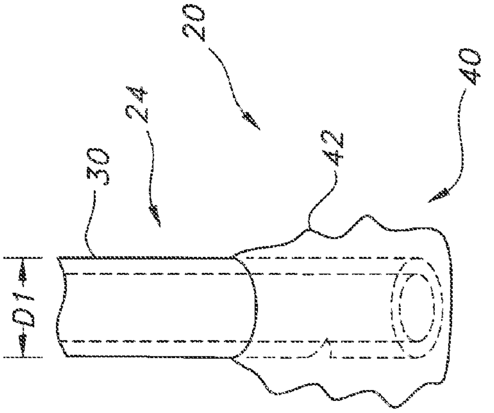
FIG. 2B is a perspective view of a detail of an exemplary inflatable retention system shown in FIG. 2A.
Figure 2A:
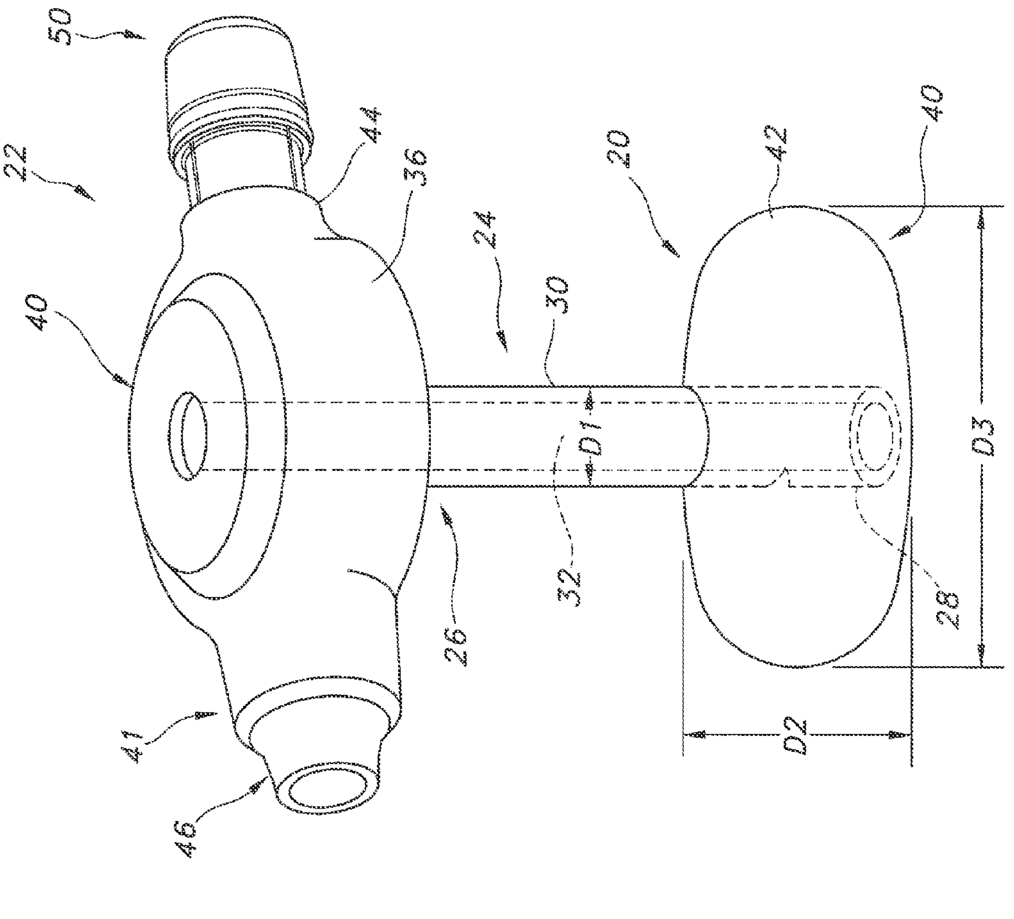
FIG. 2A is a perspective view of an exemplary inflatable retention system for an enteral feeding tube assembly.
Figure 4:
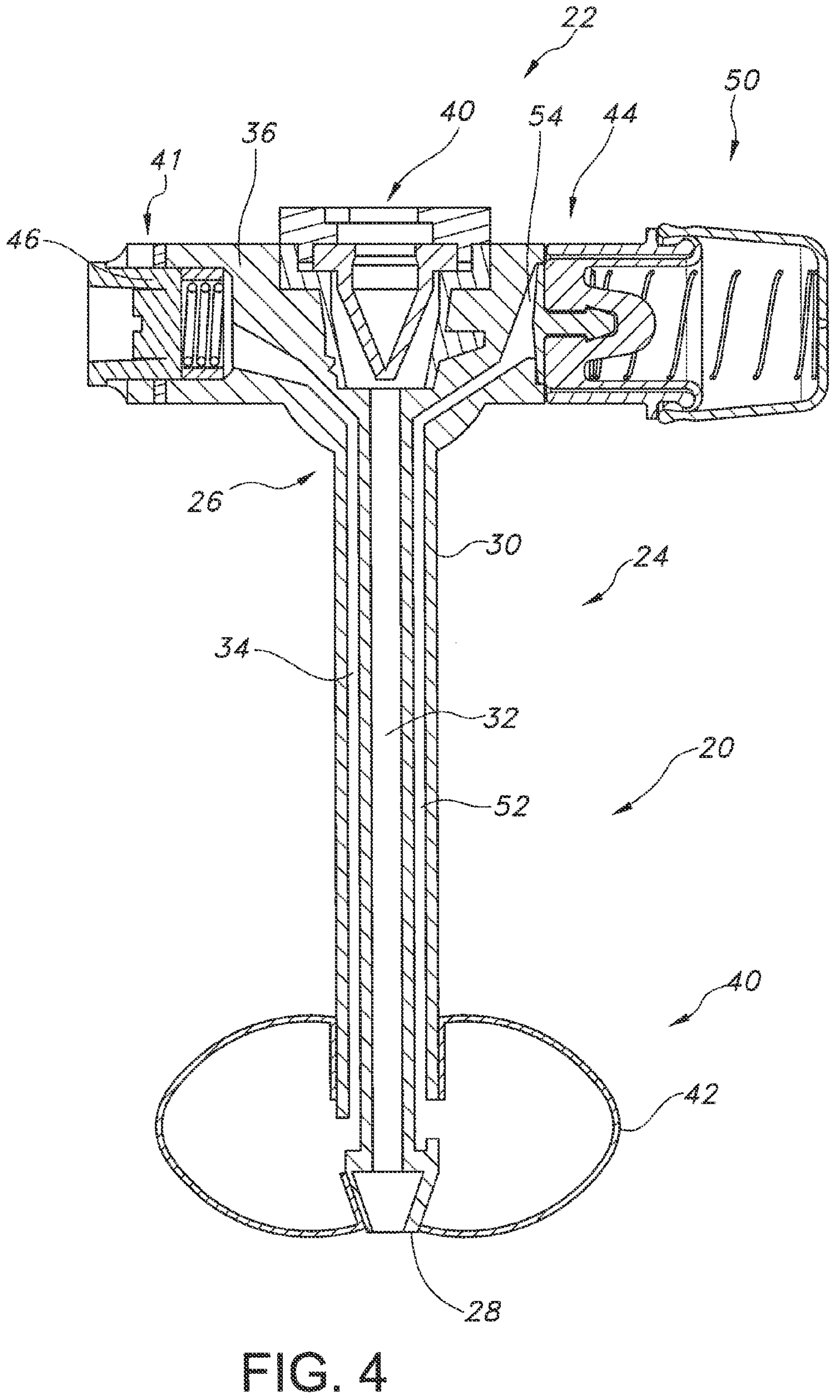
FIG. 4 is a side view illustrating a cross-section of an exemplary enteral feeding catheter assembly incorporating an exemplary inflatable retention system.

Turning now to the drawings, the present invention is generally illustrated in FIG. 2A though FIG. 4. There is shown at FIG. 2A an inflatable retention system 20 for an enteral feeding tube device 22. The retention system 20 includes a tube 24 having a proximal end 26, a distal end 28, an external tube diameter represented by "D1". The tube 24 has tube walls 30 defining a feeding lumen 32 and an inflation lumen 34. The system 20 also includes an inflatable balloon 40 located at the distal end 28 of the tube 24 in fluid communication with the inflation lumen 32. The balloon 40 has thin, flexible walls 42, a predetermined spheroid shape and a reserve volume at which a fluid is under no pressure. Desirably, the balloon 40 has a predetermined fill volume, and a reserve volume that is less than the predetermined fill volume and at which a fluid in the balloon is under no pressure.

The tube may have an external tube diameter "D1" that may range from about 3 mm to about 9 mm depending on the size of the feeding tube, the stoma size and details of the patient. The balloon may have a diameter of from about 15 mm to about 30 mm at a major axis of the spheroid when inflated to the predetermined fill volume. The ratio of this balloon diameter to the external tube diameter is desirably greater than three. For example, the ratio of this balloon diameter to the external tube diameter is desirably greater than about 3.5. As another example, the ratio of this balloon diameter to the external tube diameter is desirably greater than about 4. As yet another example, the ratio of this balloon diameter to the external tube diameter is desirably greater than about 4.5. As another example, the ratio of this balloon diameter to the external tube diameter is desirably greater than about 5.

The tube is desirably formed of a material that is generally harder, tougher and/or less elastic than conventional silicone tubing used for enteral feeding tubes. As an example, the tube may be formed of a material having a Shore Hardness of from about 65 A to about 80 A and an ultimate tensile of between about 2500 to about 6000 pounds$_f$ per square inch (psi). While such a material may have a tensile force of 300 psi at an elongation about 100 percent and/or a tensile force of 500 psi at an elongation about 200 percent (which may be similar to some conventional silicone elastomeric materials) the greater hardness and ultimate tensile is thought to make the tube more resistant to stretching while still retaining flexibility. Exemplary materials include thermoplastic polyurethanes such as TECOFLEX® medical-grade aliphatic polyether polyurethanes available from Lubrizol Advanced Materials, Inc., Thermedics™ Polymer Products, Wilmington, Mass. For example, TECOFLEX® EG-80A has been found to work particularly well. Table 1 below provides some representative properties for TECOFLEX® EG-80A.

TABLE 1

| | ASTM Test | TECOFLEX ® EG-80A |
|---|---|---|
| Durometer (Shore Hardness) | D2240 | 72A |
| Specific Gravity | D792 | 1.04 |
| Flexural Modulus (psi) | D790 | 1,000 |
| Ultimate Tensile (psi) | D412 | 5,800 |
| Ultimate Elongation (%) | D412 | 660 |
| Tensile (psi) at 100% Elongation | D412 | 300 |
| Tensile (psi) at 200% Elongation | D412 | 500 |
| Tensile (psi) at 300% Elongation | D412 | 800 |

As noted above, the material of the tube may desirably have a Shore Hardness of from about 65 A to about 80 A. The Shore Hardness testing of plastics is most commonly measured by the Shore (Durometer) test using either the Shore A or Shore D scale. The Shore A scale is used for "softer" rubbers while the Shore D scale is used for "harder" ones. The Shore A Hardness is the relative hardness of elastic materials such as rubber or soft plastics can be determined with an instrument called a Shore A Durometer. If the indenter completely penetrates the sample, a reading of 0 is obtained, and if no penetration occurs, a reading of 100 results. The reading is dimensionless.

The Shore hardness is measured with an apparatus known as a Durometer and is sometimes also referred to as Durometer Hardness. The hardness value is determined by the penetration of the Durometer indenter foot into the sample. Because of the resilience of rubbers and plastics, the hardness reading may change over time so the indentation time is sometimes reported along with the hardness number. The ASTM test number is ASTM D2240 while the analogous ISO test method is ISO 868.

A characteristic feature of the inflatable balloon 40 is that is has a predetermined shape and may have a predetermined fill volume. Generally speaking, a first phase of expansion of a balloon having an initially collapsed or crumpled state as generally illustrated in FIG. 2B continues to the point in which the material that forms the balloon is smooth and unfolded as generally illustrated in FIG. 2A, but while the material of the balloon is in a non-distended or unstretched state. At this phase, fluid in the balloon is under no pressure. A second phase of expansion of such a balloon is inflation that generates stretching or distending of the material of the balloon. The predetermined fill volume is a volume in a range having a lower limit at the volume in which the material that forms the balloon first becomes smooth, is unfolded and under a pressure but prior to any meaningful stretching or distending of that material and an upper limit that is no more than 50% greater in volume than the lower limit. In other words, the predetermined fill volume is a volume in a range with a lower limit at the balloon's transition from a non-distended state to a distended state and a upper limit that is no more than about 1.5 times (i.e., about fifty percent (50%) greater than) the volume of the balloon at the transition from a non-distended state to a distended state. The volume at the lower limit of this range where the pressure of the fluid in the balloon is essentially zero is the upper limit of the reserve volume.

Stated differently, the predetermined fill volume is desirably from about the upper limit of the reserve volume (i.e., just above the upper limit of the reserve volume) to about 1.5 times greater than the upper limit of the reserve volume (i.e., about the upper limit of the reserve volume to about 50 percent greater than the volume of the balloon at the transition from its non-distended state to its distended state). For example, the predetermined fill volume may be from about 1.01 to about 1.4 times greater than the upper limit of the reserve volume (i.e., about 1 percent to about 40 percent greater than the volume of the balloon at the transition from its non-distended state to its distended state). As another example, the predetermined fill volume may be from about 1.5 to about 1.3 times greater than the upper limit of the reserve volume (i.e., about 5 percent to about 30 percent greater than the volume of the balloon at the transition from its non-distended state to its distended state).

Another way to describe an inflatable balloon having a predetermined fill volume is as an impervious, very flexible bag or container having a relatively fixed size (i.e., fixed volume). When the balloon (i.e., bag) is empty, it is essentially in a collapsed state and has the potential to be filled with a fluid up to its fixed size. Filling is accomplished by introducing fluid into the balloon through the inflation valve of the enteral feeding assembly. As the balloon receives increasing volumes of fluid, the balloon transforms from a collapsed state to a non-distended state that generally corresponds to the particular profile of a balloon typically generated during the manufacture of the balloon in a molding, blowing, casting or similar process. Essentially no pressure is required to fill the balloon other than to drive the liquid through the inflation lumen and unfold the balloon because the material forming the balloon is not stretched or distended to reach its fixed or predetermined size. The "reserve volume" of the balloon is found at or below the transition between the balloon's non-distended state and distended state (before the fluid in the balloon is under pressure). As discussed above, the reserve volume has an upper limit. The reserve volume also has a lower limit which, for purposes of the present invention, is always more than 0.5 milliliters. A reserve volume may desirably be described in terms of a percentage of the upper limit. For example, a reserve volume may be described as volume that is, for example, 50 percent of the upper limit of the reserve volume. More particular, if the upper limit of the reserve volume is 2 milliliters, a reserve volume may be described as a volume that is 50 percent of the upper limit of the reserve volume (i.e., 1 milliliter). The pressure of fluid in the balloon increases when the balloon is filled past its non-distended state (i.e., the upper limit of the reserve volume). The pressure of fluid in the balloon increases in a substantially linear relationship with additional increases in the volume of the balloon.

The predetermined fill volume of the balloon desirably corresponds to a fluid pressure in the balloon between 2 to about 9 pounds per square inch (14 to 64 kilopascals). For example, the predetermined fill volume of the balloon may desirably correspond to a fluid pressure in the balloon between 2 to about 7 pounds per square inch (14 to 49 kilopascals). As another example, the predetermined fill volume of the balloon may desirably correspond to a fluid pressure in the balloon between 2 to about 5 pounds per square inch (14 to 35 kilopascals). The retention system is particularly advantageous for balloons having a predetermined fill volume at relatively low pressures (e.g., 4 pounds per square inch (28 kilopascals) or less). In another aspect of the invention, the predetermined fill volume may be from about 2 milliliters to about 8 milliliters. For example, the predetermined fill volume may be from about 2 milliliters to about 6 milliliters. As another example, the predetermined fill volume may be from about 2 milliliters to about 5 milliliters. As yet another example, the predetermined fill volume may be from about 2 milliliters to about 4 milliliters. The retention system is particularly advantageous for balloons having a predetermined fill volume from about 2 milliliters to about 3 milliliters.

According to the invention, when the balloon is inflated with a fluid beyond the reserve volume to pressurize fluid in the balloon, the material of the balloon assumes a stable spheroid shape and exhibits a substantially linear pressure versus volume curve to at least the predetermined fill volume. Generally speaking, a spheroid is an ellipsoid in which two radii (or diameters) are equal. The balloon desirably has an oblate spheroid shape (e.g., a disc shape) when inflated beyond the reserve volume. In contrast, a prolate spheroid shape (e.g., a rugby ball or American football shape) is considered undesirable.

In an aspect of the invention and as illustrated in FIG. 2A, the balloon may desirably an oblate spheroid in which the ratio of the diameter of the balloon along its minor axis "D2" to the diameter of the balloon along its major axis "D3" may be from about 0.45 to about 0.65. That is, the diameter of the balloon in the axial dimension that is parallel to the feeding tube (i.e., "D2") to which the balloon is attached in comparison to the diameter of the balloon in the dimension that is perpendicular to the feeding tube (i.e., "D3") may be from about 0.45 to about 0.65. More desirably, the ratio may be from about 0.5 to about 0.6.

The stability of the spheroid shape can be characterized by a resistance to deformation such as, for example, distortion in shape due to application of a force to a balloon inflated past its reserve volume. It is believed that the increased stability or resistance to deformation provided by the balloons and to some extent the tube of the inflatable retention system of the present invention helps the retention system resist being pulled through a stoma. This stability of the balloon (or deformation of the balloon) can be measured as generally described in the Examples discussed in this Specification. In Example 1—Retention Force Testing, the stability of the balloon may be characterized utilizing a Retention Force Test. In Example 3—Balloon Stability, the stability of the balloon may be characterized utilizing testing which measures changes in the diameter of the balloon as a result of a force applied utilizing a circular foot and weights of up to about 325 grams. While some lack of stability or deformation is desirable to prevent trauma to the patient at the stoma site, conventional silicone balloons and many other types of retention devices deform substantially allowing the retention portion of an enteral feeding tube device to unintentionally be pulled through the stoma.

Generally speaking, when inflated to its predetermined fill volume the balloon portion of the inflatable retention system should remain stable and deform less than about 15% when subjected to distorting or deforming forces such as might be encountered when the indwelling retention portion of an enteral feeding tube device is unintentionally being pulled through a stoma, for example as characterized by the procedure of Example 3 if not other techniques including but not limited to Example 1. Desirably, when inflated to its predetermined fill volume the balloon portion of the inflatable retention system should remain stable and deform less than about 10%, as may be characterized, for example, by the procedure of Example 3. In an aspect of the invention, when inflated to a volume that is greater than its predetermined fill volume the balloon portion of the inflatable retention system should deform less than about 15% (as may be characterized, for example, by the procedure of Example 3). For example, when the balloon is inflated to a volume that is up to about 40% greater than its predetermined fill volume, the balloon should remain stable and deform less than about 10 percent (e.g., from about 2.5 to about 10%) as may be characterized, for example, by the procedure of Example 3. More desirably, when the balloon is inflated to a volume that is up to about 25% greater than its predetermined fill volume the balloon of the inflatable retention system should remain stable and deform less than about 15% (as may be characterized, for example, by the procedure of Example 3).

In another aspect of the invention, the balloon walls of the inflatable retention system are sufficiently thin (e.g., between 5 micrometers and about 100 micrometers) such that the balloon will burst or a portion of the balloon will detach from the tube when the distorting or deforming forces, such as might be encountered when the indwelling retention portion of an enteral feeding tube device is unintentionally being pulled through a stoma, become sufficiently large. The failure of the balloon portion of the inflatable retention system serves as a failsafe to prevent trauma to the patient. The burst pressure or detachment pressure can be engineered into the inflatable retention system. For example, a burst pressure or detachment pressure corresponding to a retention force (i.e., peak load) of about 8 to about 14 pounds force as may be measured by, for example, the Retention Force Test described in this Specification and in Example 1—Retention Force Testing.

Various materials may used to form the inflatable balloon having a predetermined fill volume. These materials include, but are not limited to, polyurethane (PU), low-density polyethylene (LDPE), polyvinyl chloride (PVC), polyamide (PA), or polyethylene teraphthalate (PETP). Additionally, copolymer admixtures for modifying the characteristics of the material may be used, for example a low density polyethylene and ethylene-vinyl acetate copolymer (LDPE-EVA), or blends of the above mentioned materials (e.g. PU with PVC or PU with PA) would be considered suitable for forming the inflatable balloon having a predetermined fill volume. An exemplary material is a thermoplastic polyurethane elastomeric material identified as Pellethane® which is available from Lubrizol Advanced Materials, Inc.—Thermedics™ Polymer Products, Wilmington, Mass. A particularly useful thermoplastic polyurethane elastomeric material is Pellethane® 2363-90A TPU. Other materials would also be suitable so long as they exhibit properties enabling them to be processed into an inflatable retention balloon having thin walls on the order of about 5 to about 100 micrometers as measured in the central region of the balloon. This thickness may be determined by conventional techniques utilizing a digital contact device such as, for example a Mitutoyo Litematic Digimatic Measuring Unit in accordance with the appropriate standardized tests. Desirably, the balloons may have thin walls desirably in a range of between about 5 to about 50 micrometers, even more desirably, between about 5 to about 25 micrometers.

Suitable materials should possess properties enabling them to be processed into an inflatable retention balloon having micro thin walls which does not deform elastically to such a degree that to the balloon can slip through an opening. In contrast, conventional silicone balloons have wall thicknesses of about 250 micrometers or even greater and generally deform elastically to such a degree that to the silicone balloon can slip through an opening such as a stoma. The materials described above as useful for the inflatable retention balloon having micro thin walls may be manufactured into a balloon utilizing blow molding techniques described at, for example, commonly assigned U.S. Patent Application Publication No. 2009/0209908 for "Tubular Workpiece For Producing an Improved Balloon Cuff Tracheostomy Tube", published Aug. 20, 2009 the disclosure of which is incorporated by reference.

As illustrated in FIG. 2B not necessarily to scale, the balloon 40 desirably has a collapsed, non-inflated state such that the tube 24 and the thin, flexible walls 42 of the balloon can pass through an orifice that is not much greater than the external diameter of the tube. For example, for tubes having a French size ranging from 10 to 14 (e.g., external diameters ranging from about 3.3 mm to about 4.6 mm), the balloon desirably has a collapsed, non-inflated state such that the tube and the thin, flexible walls of the balloon can pass through an orifice that is not more than about 20 percent greater than the external diameter of the tube. As another example, with tubes having a French size ranging from 10 to 14, the balloon desirably has a collapsed, non-inflated state such that the tube and the thin, flexible walls of the balloon can pass through an orifice that is from about 12 percent greater to not more than about 20 percent greater than the external diameter of the tube. For tubes having a French size ranging from 16 to 24 (e.g., external diameters ranging from about 5.3 mm to about 8.0 mm), the balloon desirably has a collapsed, non-inflated state such that the tube and the thin, flexible walls of the balloon can pass through an orifice that is not more than about 10 percent greater than the external diameter of the tube. As an example, with tubes having a French size ranging from 16 to 24 (e.g., external diameters ranging from about 5.3 mm to about 8.0 mm), the balloon desirably has a collapsed, non-inflated state such that the tube and the thin, flexible walls of the balloon can pass through an orifice that is from about 3 percent to not more than about 10 percent greater than the external diameter of the tube.

More particularly, the balloons used in the inflatable retention system of the present invention have been found to increase the tube diameter at the location where they are attached to the tube by only about two French sizes (~0.666 mm) for tubes having French sizes ranging from 10 to 14. Moreover, balloons used in the inflatable retention system of the present invention increase the tube diameter by only about one French size (~0.333 mm) for tubes having French sizes ranging from 16 to 24. In contrast, conventional silicone balloons are much thicker and have been found to increase the tube diameter at the location where they are attached to the tube by about four French sizes (~1.333 mm) for tubes having French sizes ranging from 10 to 24. Table 2 below provides a summary of the increase in the tube diameter at the location where the balloons are attached to different size tubes. More particularly, Table 2 provides the results for the balloons of the inventive inflatable retention system of the present invention (e.g., polyurethane balloons) in comparison to conventional silicone balloons.

TABLE 2

| Tube Size (French) | Approximate tube Diameter (mm) | Percent Diameter Increase due to Polyurethane Balloons | Percent Diameter Increase due to Conventional Silicone Balloons |
|---|---|---|---|
| 10 | 3.3 | 20.0 | 40.0 |
| 12 | 4.0 | 17.0 | 33.3 |
| 14 | 4.7 | 14.0 | 20.0 |
| 16 | 5.3 | 6.0 | 25.0 |
| 18 | 6.0 | 5.5 | 22.0 |
| 20 | 6.7 | 5.0 | 20.0 |
| 22 | 7.3 | 4.5 | 18.0 |
| 24 | 8.0 | 4.0 | 17.0 |

Figure 3A:
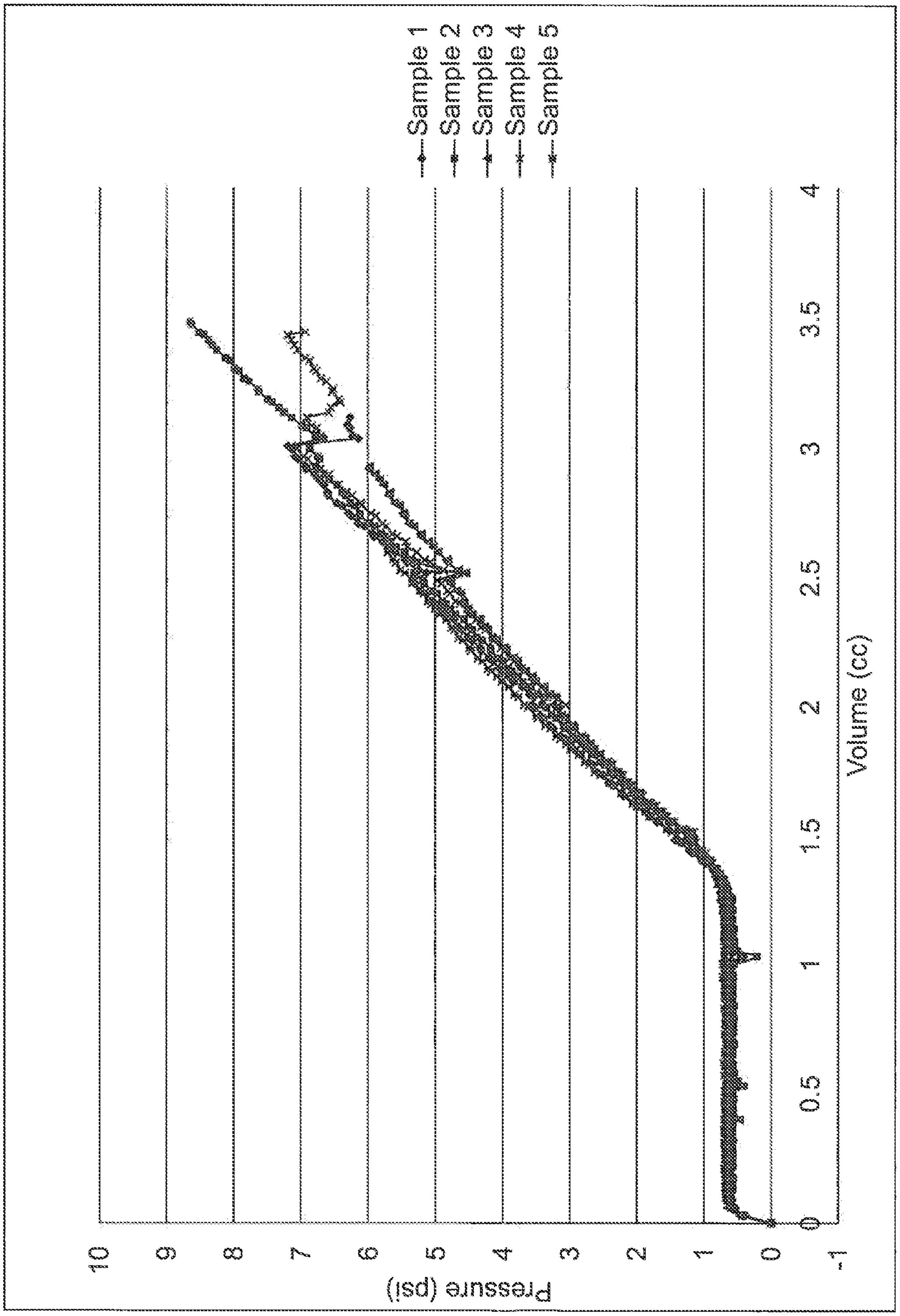
FIGS. 3A and 3B are illustrations of a feature of an exemplary inflatable retention system for an enteral feeding tube assembly.
Figure 3B:
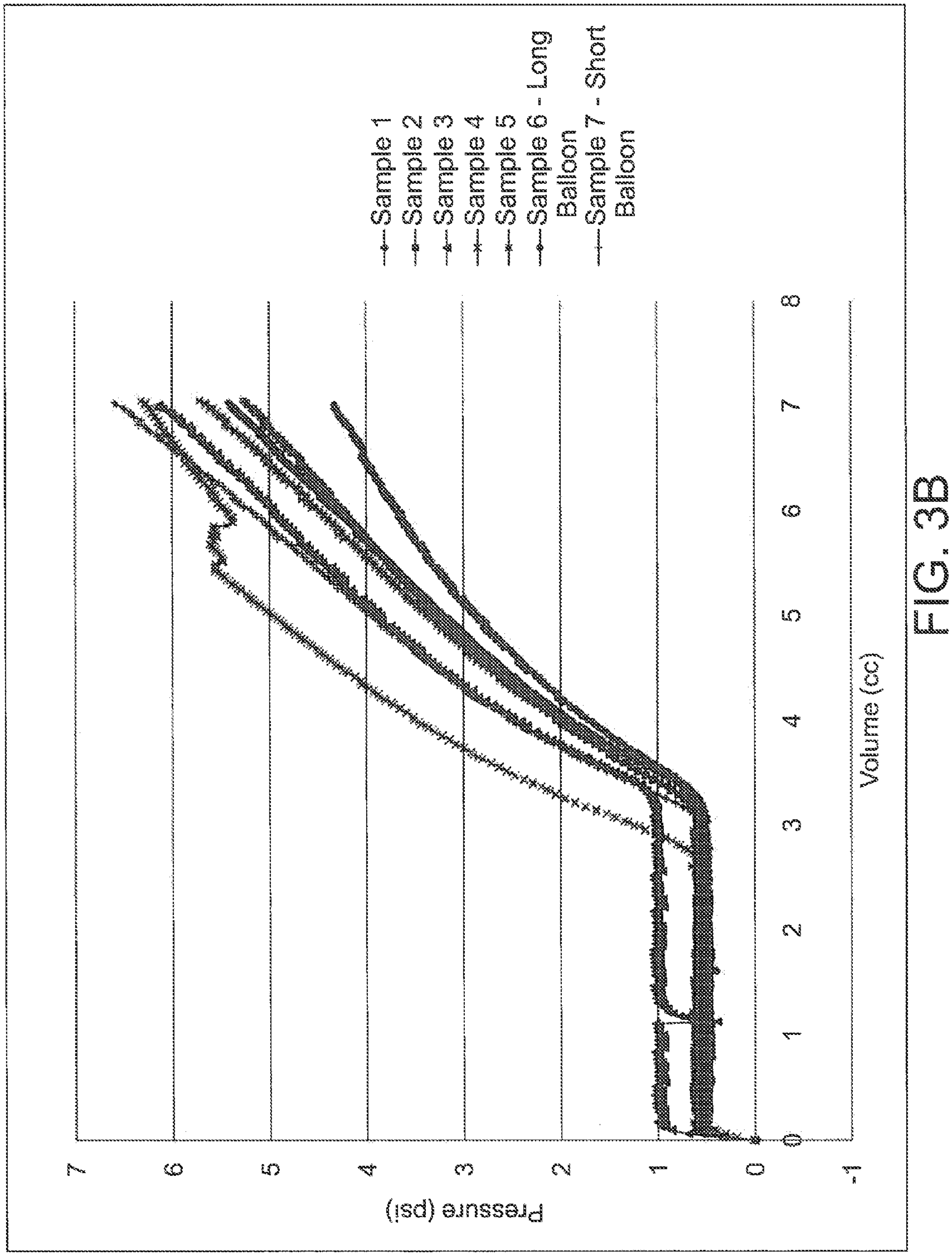

Referring now to FIGS. 3A and 3B, these figures are illustrations showing exemplary relationships between the balloon volume and the pressure of a fluid inside a balloon having a predetermined fill volume. More particularly, these illustrations highlight details about the transition between the non-distended state and distended state of an exemplary balloon used in the inflatable retention system of the present invention. FIG. 3A illustrates the relationship between pressure and volume for five samples of balloons having a predetermined fill volume of approximately two (2) milliliters. As can be seen in FIG. 3A, the pressure profiles are relatively negligible during filling of the balloons to the upper limit of the reserve volume. The slight pressure that is encountered at volumes between zero (0) and about 1.5 milliliters is due to the driving force needed to get the fluid through the inflation lumen and to unfold the collapsed balloon. At the transition from the non-distended state to the distended state which occurs at a volume just above about 1.5 milliliters (i.e., about 1.6 to about 1.7 milliliters), the pressures begins to increase linearly.

FIG. 3B illustrates the relationship between pressure and volume for seven samples of balloons having a predetermined fill volume of approximately 5 milliliters. As can be seen in FIG. 3B, the pressure profiles are relatively negligible during filling of the balloons to the upper limit of the reserve volume. The slight pressure that is encountered at volumes between 0 and about 3.5 cc (milliliters) is due to the driving force needed to get the fluid through the inflation lumen and to unfold the collapsed balloon. At the transition from the non-distended state to the distended state which occurs at a volume just above about 3.5 milliliters (i.e., about 3.6 to about 3.7 milliliters), the pressures begins in to increase linearly.

These balloons are markedly different from conventional elastic balloons made of materials that stretch from a relaxed or un-stretched condition to continuously stretched or distended conditions under increasingly higher pressures to ten times to even twenty times or more of their initial un-stretched dimensions to contain a volume of three (3) to five (5) milliliters and a maximum volume that typically ranges between about eight (8) to about ten (10) milliliters. In many instances, such elastic balloons may be further filled to contain greater volumes without significant pressure increases and resistance to overfilling; this is because of the elastic stretching of the material of the balloon. While it is possible to make an elastic balloon that has a shape or volume even when it is not inflated, such an elastic balloon would have little or no practical use for most medical devices and especially as retainer balloons for enteral feeding tubes, because such a balloon presents additional volume and difficulty when passed through an opening such as a stoma.

Figure 1C:
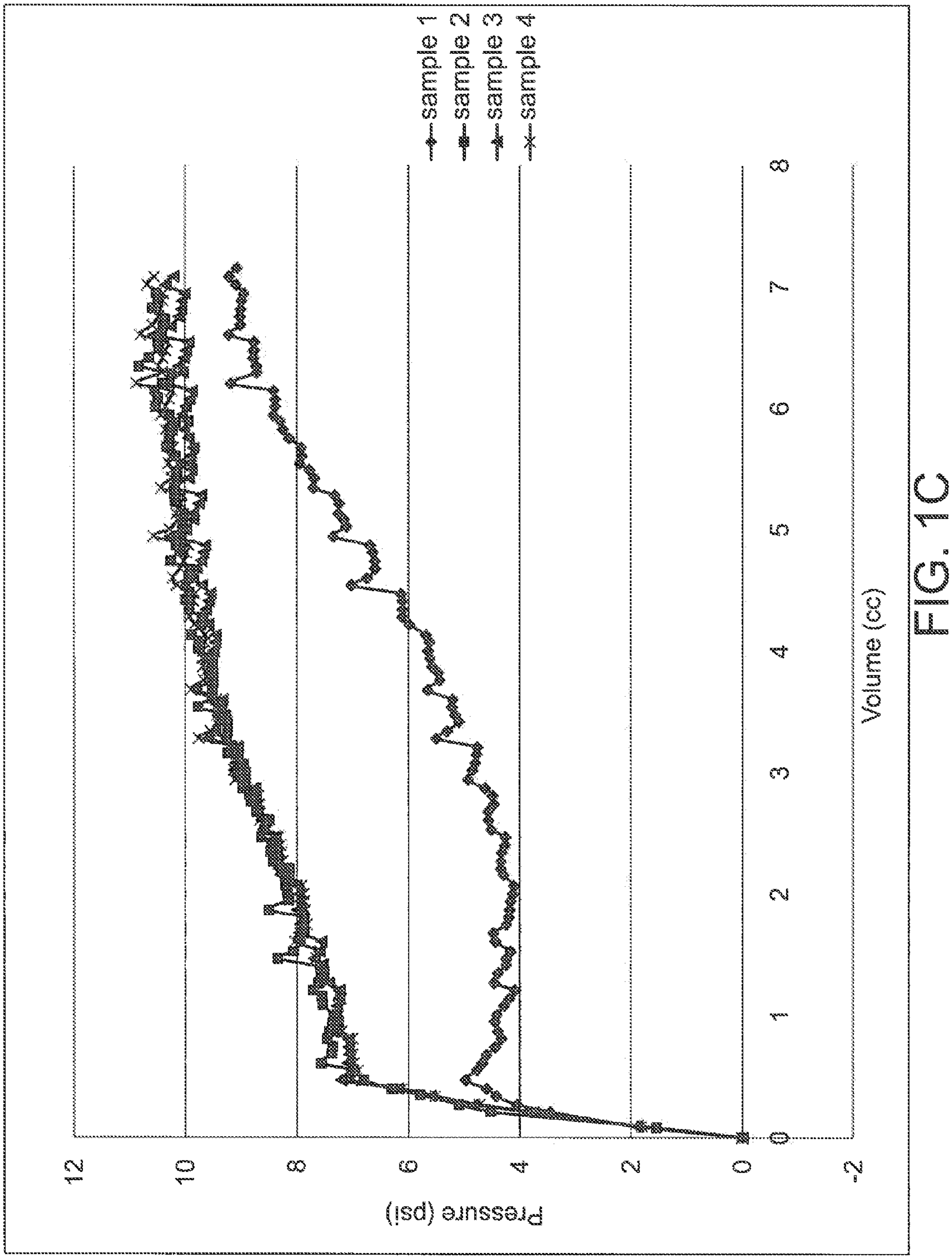
FIG. 1C is an illustration of a feature of a conventional prior art device.

As noted previously, the relationship between pressure and volume during the inflation of an elastic retainer balloon made of conventional "soft" or elastomeric medical grade silicone is illustrated in FIG. 1C. As can be seen in FIG. 1C, elastic balloons lack an obvious transition from a non-distended state to a distended state. While such a transition may exist, it likely would occur only during the earliest introduction of pressure to initiate stretching or continuous distension of the material of the balloon and would be far below the final deployed volume of the balloon. Referring to FIG. 1C, an initial pressure change from zero or negligible pressure to between about 4 to 7 pounds per square inch (28 to 48 kilopascals) is needed to continuously stretch such exemplary conventional retainer balloons to a volume of even 1 milliliter. A subsequent pressure between about 5 to 10 pounds per square inch (34 to 69 kilopascals) is needed to continuously stretch such conventional "soft" or elastomeric medical grade silicone balloons to a volume of about 3 milliliters or greater. While it may be possible to make some alterations to the distension or stretch characteristics of such conventional elastic balloons by modifying properties of the elastomeric materials or the thicknesses of the balloon walls, the pressure and volume relationship illustrated by FIG. 1C is generally representative. It is notable that the pressure and volume relationship can be characterized as non-linear.

Another important characteristic of such conventional "soft" or elastomeric balloons is that the energy used to stretch the material of the balloon ten times or even twenty times or more from its initial un-stretched dimensions is retained or stored by the stretched elastomeric material. This stretched material exerts a retraction or recovery force that seeks to take the dimensions of the balloon substantially or completely back to its original un-stretched dimensions. Accordingly, if there is a leak or breach in the balloon or in another part of the system allowing fluid to escape, the pressure against the fluid in the balloon generated by the material of the balloon as it retracts will tend to empty the balloon very quickly.

It should also be noted that the inflatable balloons used in the retention assembly the present invention are readily distinguishable from non-compliant balloons such as those used for vascular procedures like angioplasty. Such non-compliant balloons are formed of a relatively stiff material that is often reinforced to provide dimensional stability upon inflation at several atmospheres of pressure (e.g., a pressure of 3-15 atmospheres where 1 atmosphere is equal to about 14.7 $lbs_f$ per square inch or 760 torr or about 100 kilopascals). See, for example, U.S. Pat. No. 6,977,103 for "Dimensionally Stable Balloons" issued Dec. 20, 2005. The materials used for these non-compliant balloons are unsuitable for the inflatable balloons used in the retention assembly the present invention because while the materials may be molded or preformed to provide a spheroid shape, the stiffness of the materials would prevent such balloons from readily collapsing against the feed tube so they could be readily inserted through a stoma and, more particularly, collapsed after inflation so the balloon could be readily withdrawn through a stoma.

According to the invention, the retention system may further include a base located at the proximal end of the tube. The base is configured to define an opening to the catheter lumen. The base may have a first end and a second end. An inflation valve may be located on the base. The inflation valve is in fluid communication with the balloon through the inflation lumen in the tube. The base may also include an indicator. The indicator is located on the base in fluid communication with the balloon and the indicator is configured to provide a discrete visual signal that the volume of the balloon is different from a predetermined fill volume or from a reserve volume. In an aspect of the invention, the indicator may provide only a first discrete visual signal when the balloon is inflated to its predetermined fill volume and a second discrete visual signal when the fluid in the balloon is no longer under pressure, with no signal of other inflation states therebetween, whereby the second discrete visual signal provides warning that the balloon volume has reached a reserve volume.

The inflatable retention system includes the tube and the inflatable balloon as described above. The inflatable retention system may further incorporate a base and an inflation valve. The retention system may also include an indicator. The indicator may be located on the base in fluid communication with the balloon such that indicator is configured to provide a discrete visual signal that the volume of the balloon is different from a predetermined fill volume or from a reserve volume. In an aspect of the invention, the indicator may provide only a first discrete visual signal when the balloon is inflated to its predetermined fill volume and a second discrete visual signal when the fluid in the balloon is no longer under pressure, with no signal of other inflation states therebetween, whereby the second discrete visual signal provides warning that the balloon volume has reached a reserve volume.

Referring now to FIG. 4, there is illustrated an enteral feeding tube device having a base deployed outside the human body and an indwelling retainer which is deployed within a lumen of the body by insertion through a stoma from outside the body. The enteral feeding tube assembly or device incorporates the inflatable retention system 20 described above. The enteral feeding tube assembly 22 includes a tube 24 having a proximal end 26, a distal end 28, and tube walls 30 defining a feeding lumen 34. The enteral feeding assembly 22 also include a base 36 located at the proximal end 26 of the tube 24. The base 36 defines an opening 40 to the catheter lumen 32. The base itself has a first end 41 and a second end 44. The inflatable retention assembly 20 includes an inflatable balloon 40 located at a distal end of the tube. A characteristic feature of the inflatable balloon 40 is that it has a predetermined fill volume. As noted above, such inflatable balloons having a predetermined fill volume are readily distinguishable from conventional elastic balloons.

The enteral feeding assembly 22 may include an inflation valve 46 located on the base. The inflation valve 46 is in fluid communication with the balloon 40. This may be accomplished through an inflation lumen 34, defined by a portion of the wall 30 of the tube 24, extending from the balloon 40 to the inflation valve 46. An external inflation lumen or other configurations are contemplated. The inflation valve may desirably be located on the first end 41 of the base.

An indicator 50 may be located on the base 36 in fluid communication with the balloon 40. The indicator is configured to provide a discrete visual signal that the pressure of a fluid in the balloon has changed from a predetermined level of pressure. Alternatively and/or additionally, the indicator 50 may be configured to provide a discrete visual signal that the volume of the balloon 40 has changed from a predetermined volume. For example, the indicator 50 may be configured to provide a discrete visual signal that the volume of the balloon 40 is less than a predetermined fill volume.

The indicator 50 may be located on the second end 44 of the base 36. It is contemplated that the indicator 50 may be located on the first end 41 of the base fitted in parallel with the inflation valve 46 or in some other arrangement. The indicator 50 may be in fluid communication with the balloon 40 through an indicator lumen 52, defined by a portion of the wall 30 of the tube 24, extending from the balloon 40 to the indicator 50 and through a channel 54 defined in the base 36. Alternatively and/or additionally, the indicator may be in fluid communication with the balloon through the inflation lumen, defined by a portion of the wall of the catheter, extending from the balloon to the inflation valve and the indicator.

The indicator may be a pre-biased indicator. For example, the indicator may be an indicator that includes a biasing element such as described in commonly assigned U.S. patent application Ser. No. 12/645,553 for an "Enteral Feeding Catheter Assembly Incorporating An Indicator" filed on Dec. 23, 2009, the disclosure of which is incorporated by reference in its entirety. The biasing element is desirably a spring such as, for example, a coil compression spring. It is contemplated that other resilient constructions could be used as the biasing element. These include flexible, resilient foams, metal strips, volute or secateur springs, conical springs and the like. Descriptions of conical springs may be found at, for example, U.S. Pat. No. 4,111,407 for "Conical Compression Spring". Generally speaking, the biasing element is desirably a coil compression spring that may be characterized as having linear movement and a spring rate designed such that the spring rapidly deforms over a very small range of pressure to provide a very discrete signal that the pressure of a fluid in the balloon is different from the predetermined pressure of the spring.

The biasing element is desirably configured so that the indicator generates the discrete visual signal occurs over a relatively small change in the pressure of the fluid in the balloon. For example, the change in pressure sufficient to generate the discrete visual signal may be between about 0.25 pounds per square inch and about 0.75 pound per square inch. As another example, the change in pressure sufficient to e generate the discrete visual signal may be between about 0.4 pounds per square inch and about 0.6 pound per square inch. As yet another example, the change in pressure sufficient to generate the discrete visual signal may be about 0.5 pounds per square inch (approximately 3.5 kilopascals). This change in pressure is a change in relative pressure and represents a change in pressure relative to the surrounding ambient or atmospheric pressure.

If the biasing element is a spring, the spring rate of the biasing element is a linear spring rate and is expressed in terms of pounds-force per linear inch (lbs-force/inch). That is, the spring rate is the load, expressed in pounds-force, required to deflect (i.e., compress or expand) the spring by a distance of one inch. For example, if the spring rate is forty (40) lbs-force/inch, it would take ten (10) lbs-force to deflect (i.e., compress or expand) the spring 0.25 inch and it would take eighty (80) lbs-force to deflect (i.e., compress or expand) the spring two (2) inches. One (1) lb-force/inch is about 1.8 newtons/cm.

The spring rate may range from about 0.1 lbs-force/inch to about 1.0 lbs-force/inch (about 0.4 newtons/inch to about 4.5 newtons/inch or about 0.1 newtons/cm to about 1.8 newtons/cm). Desirably, the spring rate may range from about 0.13 lbs-force/inch to about 0.60 lbs-force/inch. More desirably, the spring rate may range from about 0.2 lbs-force/inch to about 0.45 lbs-force/inch. Even more desirably, the spring rate may range from about 0.25 lbs-force/inch to about 0.35 lbs-force/inch. For example, the spring rate may be about 0.3 lbs-force/inch.

During normal use of an enteral feeding assembly, a user utilizes a syringe to add sterile water or some other appropriate liquid, or in some situations, air, through the inflation valve to fill the balloon. Fluid pressure is generated by filling the balloon past the upper limit of the "reserve volume" (i.e., at the transition from its non-distended state to its distended state). As the pressure of the balloon reaches a predetermined level of pressure, the biasing element deforms. The predetermined level of pressure corresponds to a predetermined fill volume, which is a volume in a range with a lower limit at the volume of the balloon at the transition from its non-distended state to its distended state where the fluid in the balloon is first under pressure (i.e., the upper limit of the reserve volume) to an upper limit no more than about 1.5 times (i.e., 50 percent greater than) the volume of the balloon at the transition from its non-distended state to its distended state. If the indicator is incorporated in the base, the biasing element of the indicator deforms due to force (i.e., fluid pressure) communicated from the balloon through the indicator lumen (or, in some configurations, the inflation lumen). When inflated to its predetermined fill volume, the balloon generally resists deformation. Moreover, unlike conventional silicone tubes, the tube component (e.g., the tube 24 illustrated in FIGS. 2A and 4) of the present invention resists deformation due to stretching forces applied axially to the tube by the balloon. Conventional silicone tubes tend to becomes stretched axially due to due to stretching forces applied to the tube by the balloon. This is thought to make the walls of the tube thinner and more susceptible to collapse in response to pressure against the tube walls by a fluid in the balloon. Such stretching and collapse of the tube restricts the diameter of the lumen in the tube and can provide resistance to the passage of fluids such as nutritional solutions through the feeding tube. In contrast, the tube component of the present invention resists stretching and collapse of the tube that would restrict the diameter of the lumen in the tube. Moreover, since the balloons of the present invention are generally stable at lower pressures than conventional silicone balloons, the balloons of the retention system of the present invention present less stretching force in the axial direction on the tube as well as less force against the wall of the tube.

A better understanding of the above and many other features and advantages of the new inflatable retention system for an enteral feeding tube and for the new enteral feeding tube assembly incorporating such an inflatable retention system may be obtained from a consideration of the Examples of the invention below, particularly if such consideration is made in conjunction with the Tables and the appended drawings.

EXAMPLES

Aspects of the improved inflatable retention assembly were evaluated in the following examples and procedure.

Retention Test Procedure

This procedure describes a method for testing the force required to pull an enteral feeding tube with an indwelling retention portion through certain retention places that are subsequently described using a retention test fixture and a constant-Rate-of-Extension (CRE) tensile tester with a computer-based data acquisition and frame control system. This procedure assumes the user has a working knowledge of (CRE) tensile testers and the data collection software. This procedure approximates the forces needed to pull out enteral feeding tubes with deployed retention portions from stomas.

1.1 Tensile Tester Constant-Rate-of-Extension (CRE) tensile tester with a computer-based data acquisition and frame control system.

1.2 Load Cell Choose the appropriate type for the tensile tester being used. Use a load cell in which the majority of the peak load results fall between 10 and 90% of the capacity of the load cell. Obtain 1.1-1.2 from Instron Corporation, Canton, Mass. 02021, OR from MTS Systems Corporation, Eden Prairie, Minn. 55344-2290.

1.1.2.1 MTS Alliance RT/5 (DVC068-01)—MTS Systems Corporation.

1.1.2.2 250 N load cell (DVC068-06)—MTS Systems Corporation.

1.1.3 Grips and Faces—Pneumatic.

1.1.3.1 Top and Bottom Grips—Side-action, manual air switch.

1.1.3.2 Grip Faces—2.28"×1.5" (57.91 mm×38.09 mm) pneumatic-action serrated grips, or equivalent OR 1.1.3.3 Standard Capacity Grips and Faces—Top and bottom—use standard capacity grips and faces combination designed for a maximum load of 5000 grams. If the results approach this limit, observe the material being tested. If slippage is noticed, use the Instron grips and faces that have a 90.7-kg maximum load rating.

1.4. Test Works 4 Software or an equivalent data collection software.

Figure 5:
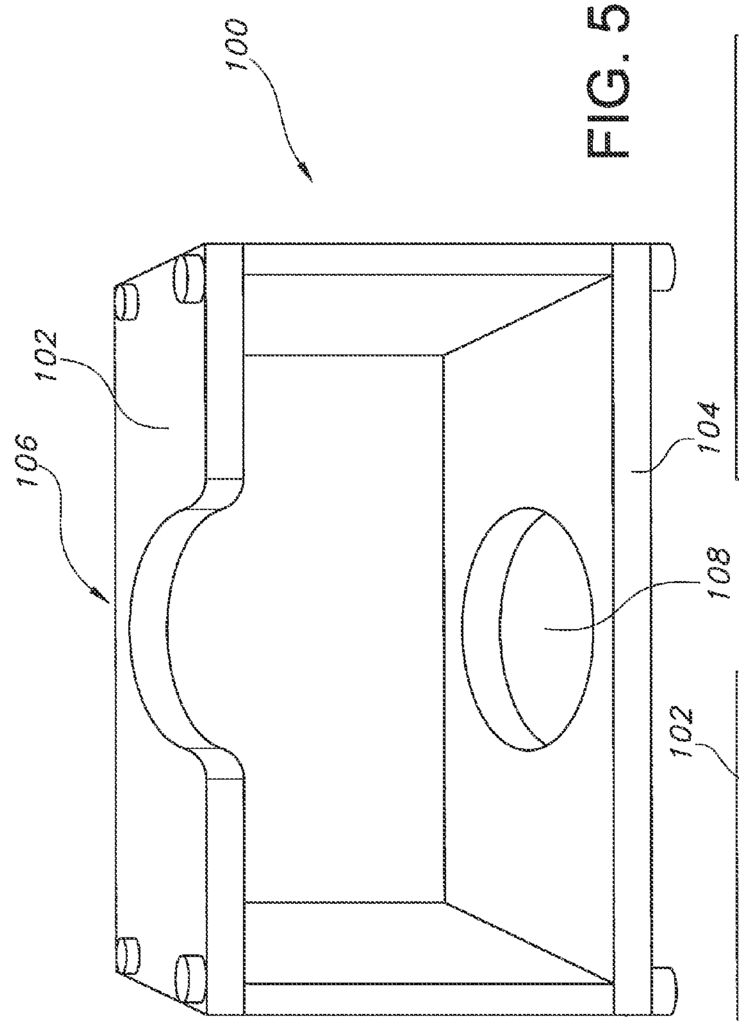
FIG. 5 is a side perspective view illustrating a detail of test equipment used to measure retention force.
Figure 7:
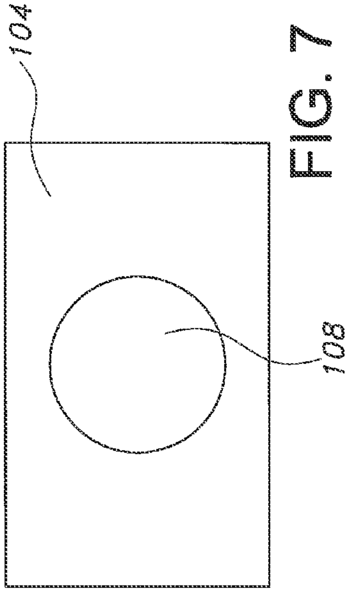
FIG. 7 is a top view illustrating a detail of a bottom plate from FIG. 5
Figure 6:
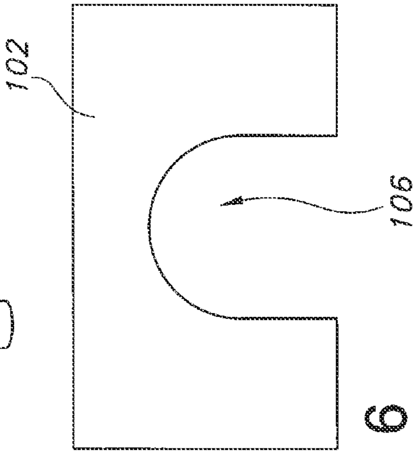
FIG. 6 is a top view illustrating a detail of a top plate from FIG. 5.

1.5. Retention test fixture (FXT-3002) as shown in FIG. 5—a box structure 100 made of rigid aluminum or steel open on two sides and having a top plate 102 and bottom plate 104. (See FIG. 5) A top plate 102 defines a semi-circular opening 106 of at least 3 inches in diameter and extending to an edge (See FIG. 6) to allow the jaws of the tensile tester to pass through unobstructed. The bottom plate 104 defines has a circular opening 108 that is about 3 inches in diameter (See FIG. 7). A metal ring approximately 3 inches in diameter is also included. The ring is used to secure retention plates over the circular opening in the bottom plate.

Figure 8:
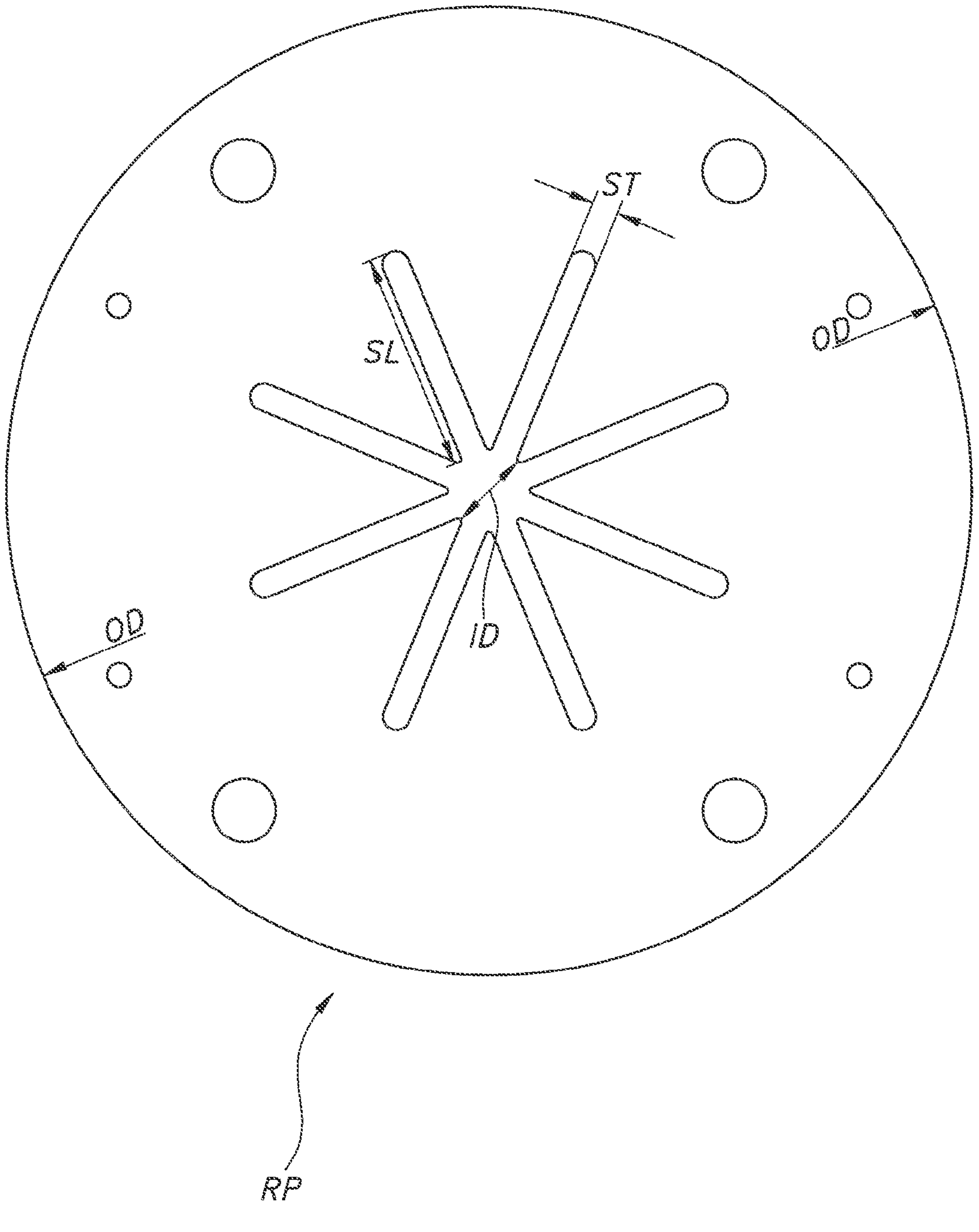
FIG. 8 is a top view illustrating a retention plate utilized in the test equipment of FIG. 5 to measure retention force.
Figure 9:
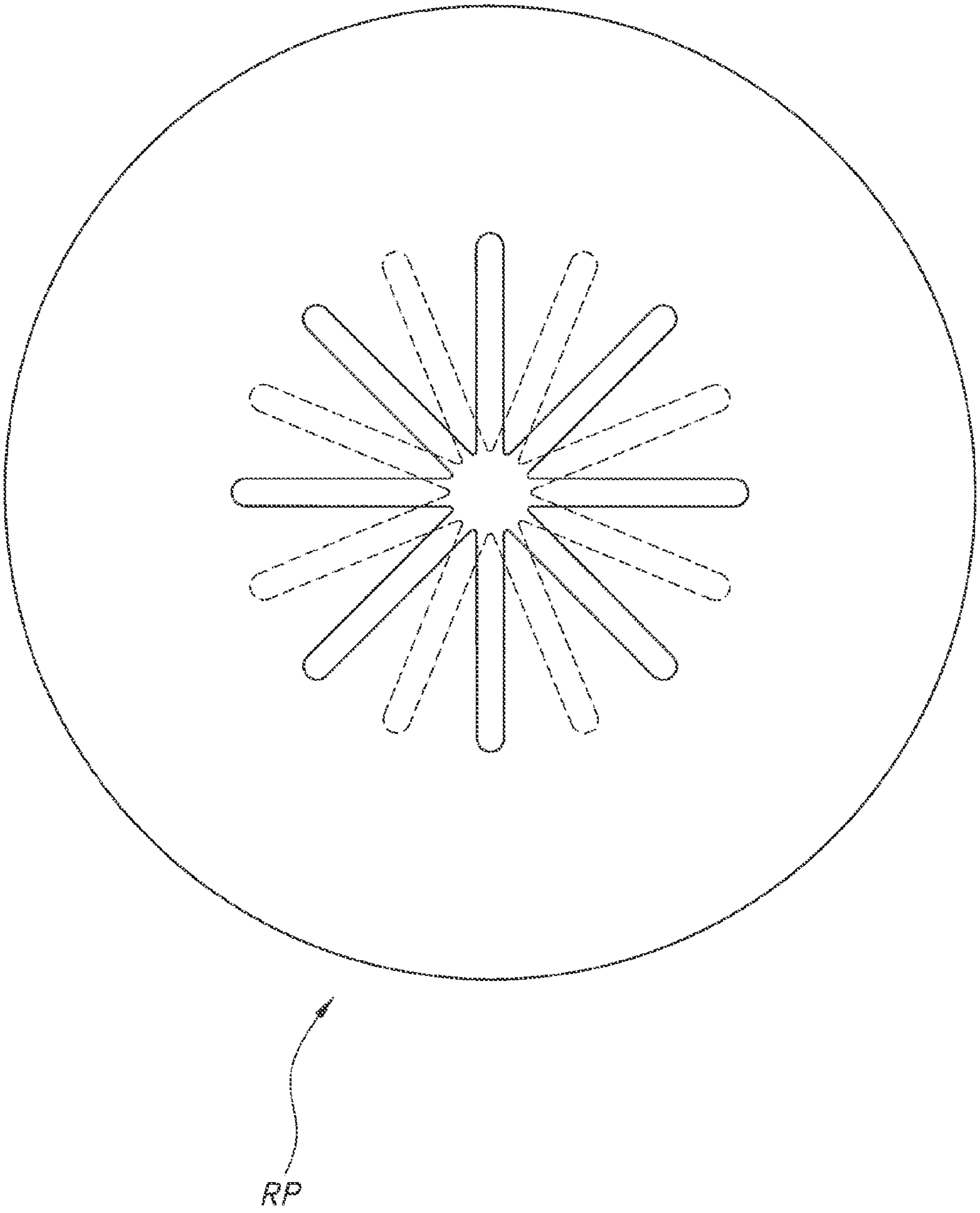
FIG. 9 is a top view illustrating two overlapped retention plates to highlight the offset of the slits as they are utilized in the test equipment of FIG. 5 to measure retention force.

1.6. Appropriate sized retention plates (see Table 3) made of Skived Sheet Teflon® polytetrafluoroethylene (PTFE) G400. Slots in the sheets were laser cut. An individual retention plate "RP" is illustrated in FIG. 8. Each test requires two retention plates. A first plate is places in a mount and a second plate is placed over the first plate so the slits are offset by about 22.5 degrees. (See FIG. 9).

TABLE 3

| French Size | Inner Circle Diameter (in, +5%) | Slit Thickness (in) | Slit Length (in) | Outer Diameter (in) | Plate Thickness (in) |
|---|---|---|---|---|---|
| 10 | 0.153 | 0.025 | 0.75 | 3.00 | 0.05 |
| 12 | 0.197 | 0.024 | 0.75 | 3.00 | 0.05 |
| 14 | 0.228 | 0.037 | 0.75 | 3.00 | 0.05 |
| 16 | 0.261 | 0.048 | 0.75 | 3.00 | 0.05 |
| 18 | 0.285 | 0.065 | 0.75 | 3.00 | 0.05 |
| 20 | 0.292 | 0.068 | 0.75 | 3.00 | 0.05 |
| 22 | 0.342 | 0.075 | 0.75 | 3.00 | 0.05 |
| 24 | 0.329 | 0.080 | 0.75 | 3.00 | 0.05 |
| 30 | 0.435 | 0.118 | 0.75 | 3.00 | 0.05 |

Referring to FIG. 8 and Table 3, the French Size refers to the enteral feeding tube size that the retention plate is sized for. The Inner Circle diameter refers to the diameter of the opening labeled "ID" in FIG. 8. The Slit Thickness refers to the width dimension labeled "ST" of the slit radiating from the Inner Circle illustrated in FIG. 8. The Slit Length refers to the length dimension labeled "SL" of the slit radiating from the Inner Circle illustrated in FIG. 8. The Outer Diameter refers to the diameter of the circular template and is labeled "OD" in FIG. 8.

2.1. Condition samples to temperature of 23° C.±3° C. for 24 hours prior to testing. Ambient temperature of testing area should remain 23° C.±3° C. and 50±5% relative humidity.

3.1. Inspect sample to ensure that there are no visible defects.

3.2. Assemble the retention test fixture (FXT-3002).

3.2.1. Align the properly sized slotted retention plates based on small alignment holes.

3.2.2. Place the plates onto FXT-3002 with the alignment holes placed over the pegs on the top of the fixture.

3.2.3. Place the metal ring on top of the plates to hold them in place.

3.2.4. Screw the entire assembly together.

3.5. Turn on the MTS tensile tester.

3.5.1. Install the 250 N load cell.

3.5.2. Install the pneumatic-action grips to the stationary bottom grip and to the moveable crosshead.

Figure 10:
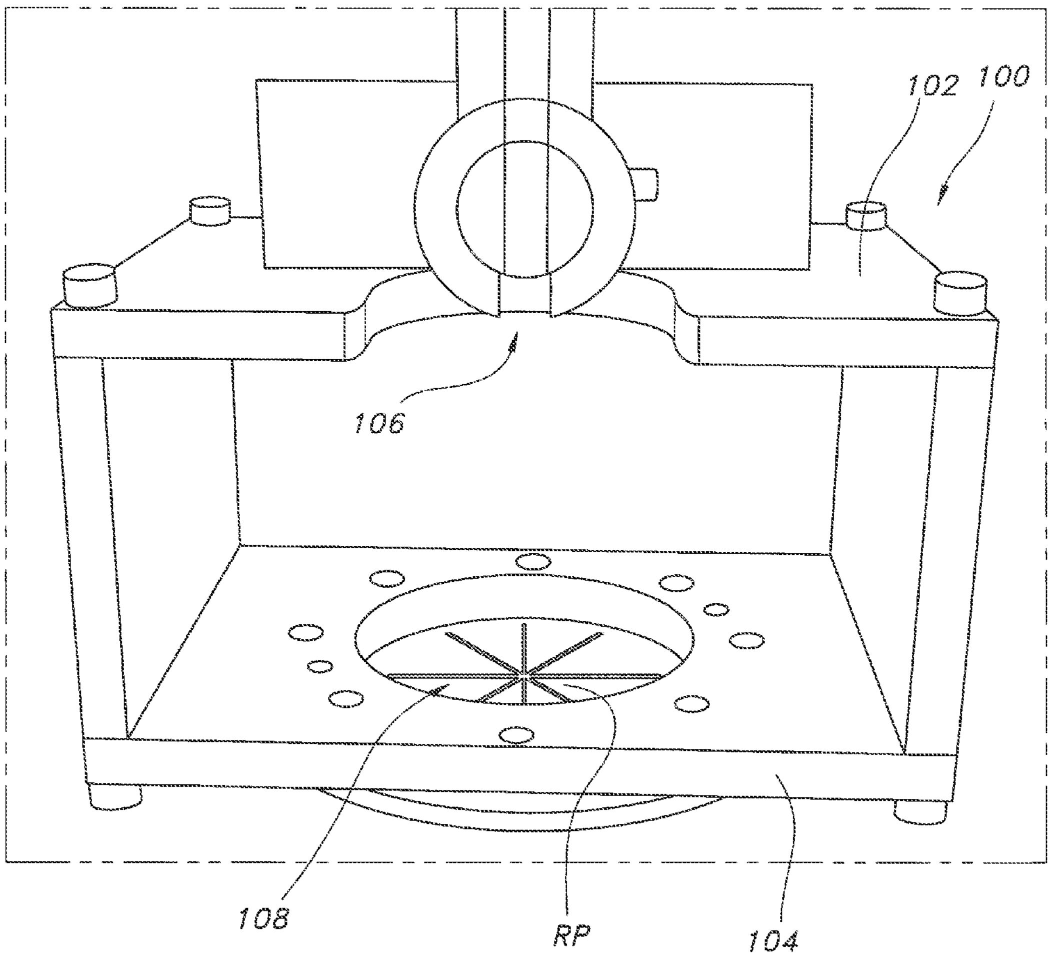
FIG. 10 is a side perspective view illustration of the test equipment configured for testing with the jaws of the tensile tester.

3.5.3. Install FXT-3002 in the top grips of the tester. See FIG. 10.

3.6. Open data collection software.

3.7. Set the testing parameters.

3.7.1. Crosshead speed to 20 in/min 3.7.2. Grip separation 3.5"

3.8. Calibrate the MTS.

Verify the tensile tester parameters meet the following specifications:

| | |
|---|---|
| Crosshead Speed | 508 mm/minute (20 inch/minute) |
| Gage Length | 25.4 mm (1 inch) |
| Load Units | Grams-force |
| Full-Scale Load | 250 N (~56.2 pound) load cell |
| Test Result | Peak load |
| Start Measurement | 25.4 mm (1 inch) |
| End Measurement | 177 mm (7 inch) |
| Endpoint | 21.6 cm (8.5 inches) |

3.9. Record the sample information (lot number, product code, product size, etc.).

4.1. Insert the device to be tested through the hole in the bottom plate of the test fixture and through the series of slotted Teflon plates.

4.2. Inflate the balloon with the recommended fill volume of water.

4.3. Clamp the device in the lower jaws of the tensile tester.

4.4. Pull test each device.

4.5. Record the failure mode and peak load of each balloon.

Example 1

Retention Testing

Samples of different enteral feeding tube devices that utilize different retention mechanisms were tested according to the Retention Test Procedure described above using the MTS Alliance RT/5 (DVC068-01) tensile tester and 250 N load cell (DVC068-06). Approximately 10 specimens of each sample were used except for Sample 2 (which has only one specimen) and an average value for the peak load (referred to as "retention force") was determined.

The following comparative samples were tested:

Sample 1—Kimberly-Clark MIC-KEY® low profile enteral feeding tube with silicone balloon—molded to be apple shaped. Size 16 French (16 Fr) feeding tube. The balloon was filled with 5 milliliters of water. During testing, the silicone balloon deformed at peak load (i.e., the "retention force") and the device pulled through the retention plate fully intact.

Sample 2—Kimberly-Clark MIC-KEY® low profile enteral feeding tube with silicone balloon—molded to be generally disc shaped as described in U.S. Patent Application Publication No. 2004/0106899. Size 18 Fr feeding tube. The balloon was filled with 5 milliliters of water. During testing, the silicone balloon burst or balloon detached from the tube at peak load (i.e., the "retention force") allowing the balloon to immediately deflate and the damaged device to pass through the retention plate.

Sample 3—Corflo® Max polyurethane PEG tube—Size 16 Fr feeding tube—lumen plugged. Sample 4—Corflo® Max polyurethane PEG tube—Size 16 Fr feeding tube—lumen open. Sample 5—Corflo® Max polyurethane PEG tube—Size 20 Fr feeding tube—lumen plugged. Sample 6—Corflo® Max polyurethane PEG tube—Size 20 Fr feeding tube—lumen open. The Corflo® Max polyurethane PEG tube is available from Corpak MedSystems, Inc., of Wheeling, Ill. Each retention component is a foam bumper encased in polyurethane material. Both size devices were tested with the "lumen open" (i.e. only the force of the foam used to retain the device) and lumen closed or "lumen plugged" (i.e. foam and air in the 'balloon' used to retain the device). The retention force reported for "lumen open" is the force required to remove the device from the stoma. The retention force reported for "lumen plugged" is the force required to accidentally remove the device from the stoma. These devices are not filled with water. During testing, these devices deformed at peak load (i.e., the "retention force") and were pulled through the retention plate fully intact.

Sample 7—Kimberly-Clark MIC® Percutaneous Endoscopic Gastrostomy (PEG) Feeding Tube with a hard plastic bumper—Size 14 Fr feeding tube. Sample 8—Kimberly-Clark MIC® Percutaneous Endoscopic Gastrostomy (PEG) Feeding Tube with a hard plastic bumper—Size 20 Fr feeding tube. Sample 9—Kimberly-Clark MIC® Percutaneous Endoscopic Gastrostomy (PEG) Feeding Tube with a hard plastic bumper—Size 24 Fr feeding tube. These devices do not have a balloon that is filled with water. During testing, these devices deformed at peak load (i.e., the "retention force") and were pulled through the retention plate fully intact.

Sample 10—Kimberly-Clark MicroCuff® pediatric tube having a tube diameter of 3.5 mm and thin-wall polyurethane balloons. Sample 11—Kimberly-Clark MicroCuff® pediatric tube having a tube diameter of 4.0 mm and thin-wall polyurethane balloons. These devices were tested using the 16 Fr retention place which is not an exact match for a 16 Fr device; however, these two sizes are just above and just below a 16 Fr equivalent size. These samples represent a thin polyurethane balloon attached to a tube to form a prolate spheroid or "hot dog" shape aligned parallel to the axis of the tube. These balloons were filled with a volume of water sufficient to bring the diameter of the balloon to 12 millimeters. During testing, these devices deformed at peak load (i.e., the "retention force") and were pulled through the retention plate fully intact with the sole exception of one Kimberly-Clark MicroCuff® pediatric tube having a tube diameter of 4.0 mm. That specimen of the Kimberly-Clark MicroCuff® pediatric tube burst or broke.

Samples representing the inflatable retention system of the present invention were tested. These samples were in the form of a low profile enteral feeding tube similar to the Kimberly-Clark MIC-KEY® enteral feeding tube except that the feeding tube portion was formed of TECOFLEX® EG-80A available from Lubrizol Advanced Materials, Inc., and a thin-wall balloon was formed of polyurethane material identified as Pellethane® 2363-90A, available from Lubrizol Advanced Materials, Inc., Thermedics™ Polymer Products. The balloon had a disc or oblate spheroid shape in which the ratio of the diameter of the balloon along the axis parallel to the feeding tube to the diameter of the balloon along the axis perpendicular to the feeding tube (i.e., ratio of the minor axis or "longitudinal" axis to the major or "equatorial" axis) was about 0.5. The wall of the balloon was about 25 microns in thickness. Sample 12—the above described balloon attached to a 10 Fr feeding tube (non-sterile), Sample 13—the above described balloon attached to a 16 Fr feeding tube (sterilized twice in an ethylene oxide sterilization procedure). Sample 14—the above described balloon attached to a 24 Fr feeding tube (non-sterile). The Sample 12 balloon was filled with 2.5 milliliters of water for testing. The Sample 13 balloon was filled with 5 milliliters of water for testing. The Sample 14 balloon was filled with 6 milliliters of water for testing. These fill volumes of 2.5 milliliters, 5 milliliters and 6 milliliters represented the respective predetermined fill volumes for different balloons. During testing, the balloon portion of the inflatable retention system for each specimen burst or a portion of the balloon detached from the tube at peak load or "retention force" allowing the balloon to immediately deflate and the damaged device to pass through the retention plate.

Figure 11:
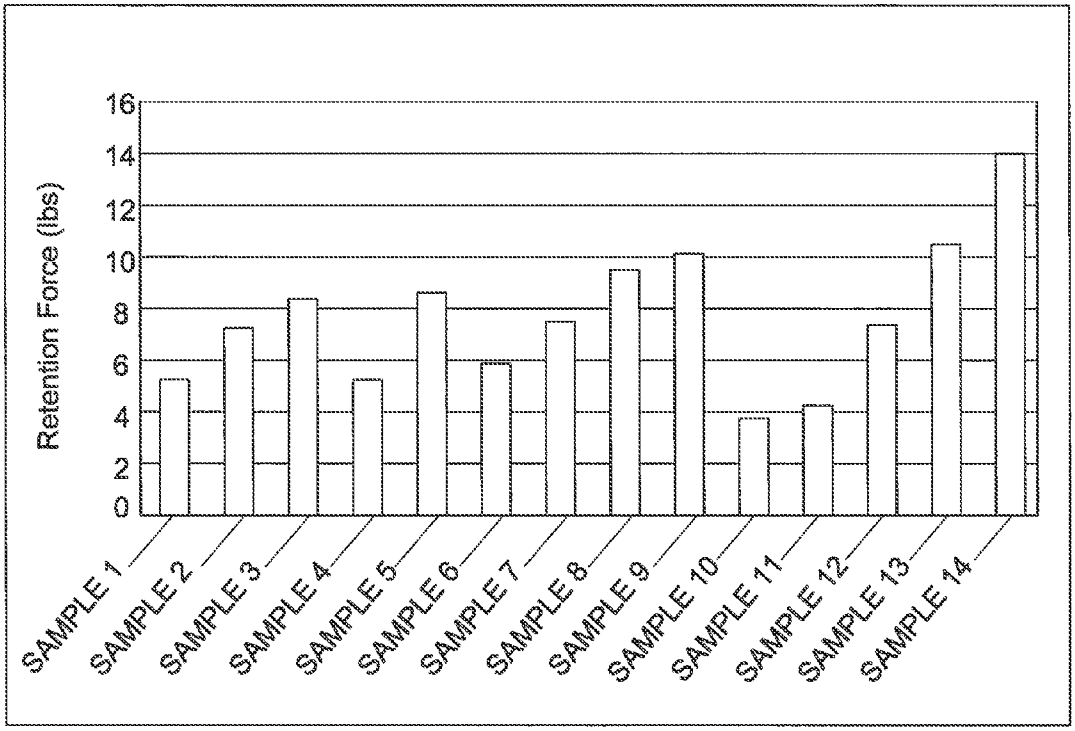
FIG. 11 is an illustration of a graph of data and information from Retention Testing of an exemplary inflatable retention system for an enteral feeding tube assembly and comparative examples.

The results of the testing are illustrated graphically in FIG. 11 which is graph representing Peak Load in units of pounds-force (labeled Retention Force) on the y-axis and the individual samples on the x-axis.

Samples 12 to 14 representing the inflatable retention system of the present invention demonstrated the highest retention forces of any device tested. Although it is much smaller, the 10 Fr device exhibits retention forces similar to those of larger conventional devices.

Sample 2 (the disc shaped silicone balloon) exhibited some improvement in retention force over Sample 1. Neither sample provides as much retention as a similarly sized inflatable retention system of the present invention (e.g., Samples 13 and 14). Notably, Sample 2 (the 18 Fr disc shaped silicone balloon) has similar retention to Sample 12 which is a much smaller 10 Fr polyurethane disc shaped balloon.

Samples 12-14 (i.e., the disc shaped polyurethane balloon and polyurethane tubes representing the inflatable retention system of the present invention) provides significantly higher retention than the prolate spheroid or 'hotdog' shaped MicroCuff® pediatric tube polyurethane.

Samples 3 through 6 (i.e., Corflo® Max polyurethane PEG tube), even with the addition of foam, provides much less retention than the inflatable retention system of the present invention. It was observed that the foam does not collapse or compact down to eliminate forces felt on the stoma when the device is removed. The foam still provides significant resistance for device removal.

Overall, the inflatable retention system of the present invention as represented by Samples 12-14 provides the greatest device retention when in the inflated state compared to other retention options. Additionally, it provides little force during device insertion and removal when the balloon is in an uninflated condition.

Example 2

Retention Diameter/Tube Diameter

The maximum diameter in the perpendicular direction from the axis of the tube of each retention portion of the Samples from Example 1 (with the exception of Sample 2) was measured. For the devices that require inflation, the devices were inflated with the volume of water specified in Example 1 with the exception of Samples 10 and 11 which were inflated to a diameter of 12 millimeters which represents the fully extended or distended state of the balloon on that device. The diameter of the tube was measured in a region where the balloon or other retention device was not attached. The diameter of each tube was uniform along the length of the tube. The retention diameter was divided by the tube diameter and the ratio is reported in Table 4.

TABLE 4

| Device | Retention Diameter | Tube Diameter | Retention Diameter-Tube Diameter Ratio |
|---|---|---|---|
| Sample 1 - 16Fr Silicone Balloon, apple shaped | 20.4 mm | 5.33 mm | 3.83 |
| Sample 2 - 18Fr Silicone Balloon, disc shaped | Sample destroyed during testing | 6 mm | N.A. |
| Samples 3 & 4 - Corflo ® Max PEG, 16Fr | 22.8 mm | 5.33 mm | 4.27 |
| Samples 5 & 6 - Corflo ® Max PEG, 20Fr | 25 mm | 6.67 mm | 3.74 |
| Sample 10 - MicroCuff ped ® ET tube, 3.5 mm | 12 mm | 5.0 mm | 2.4 |
| Sample 11 - MicroCuff ped ® ET tube, 4.0 mm | 12 mm | 5.6 mm | 2.14 |
| Sample 7 - KC PEG, 14Fr | 18.5 mm | 4.67 mm | 3.96 |
| Sample 8 - KC PEG, 20Fr | 26.2 mm | 6.67 mm | 3.93 |
| Sample 9 - KC PEG, 24Fr | 26.2 mm | 8 mm | 3.27 |
| Sample 12 - 10Fr PU Balloon, disc shaped | 18.3 mm | 3.33 mm | 5.49 |
| Sample 13 - 16Fr PU Balloon, disc shaped | 21.5 mm | 5.33 mm | 4.03 |
| Sample 14 - 24Fr PU Balloon, disc shaped | 25.9 mm | 8 mm | 3.24 |

Example 3

Balloon Stability

The balloon used as the retention component in the invention has a shape that is generalized as an oblate spheroid like other balloons used for enteral feed tubes. This shape is different from cylinder-like ones that are typical for vascular catheters, e.g. angioplasty catheters. As described previously, such generalized oblate spheroid shapes have characterizing diameters along their minor and major axes. For purposes of this Example, the greatest distance of the spheroid in the direction of its minor axis is termed the polar diameter (P) and the largest diameter in the direction of its major axis (orthogonal to the minor axis) is termed an equatorial diameter (E). In keeping with previous preferred descriptions but using the terminology of this Example, preferred shapes of the balloons of the invention have polar diameters that are significantly less than their equatorial diameters.

In making the balloons used in the invention, the balloons are preformed in cavity molds that have polar/equatorial diameter ratios ranging from 0.45 to 0.51 and are sized for use with specific feed tube diameters. Table 5 gives examples of diameter dimensions for the feed tube (French size and inch equivalent) and the dimensions of matching preformed balloons, expressed as polar and equatorial diameters, along with certain volumes in ml of water, Test Volumes. These Test Volumes are appropriate volumes for use as predetermined fill volumes. Included in Table 5 are the ratios of the polar to equatorial diameters and calculated volumes based on the formula: $4/3*\pi a2*b$, where $a=\frac{1}{2}$ the equatorial diameter and $b=\frac{1}{2}$ the polar diameter, and water as the fill media. The calculated volumes that correspond to the dimensions of each preformed balloon less the volume of the catheter segment between the balloon attachment locations also represent the respective maximum reserve volumes that are possible.

TABLE 5

| Preformed balloons suitable for the invention | | | | | | | | |
|---|---|---|---|---|---|---|---|---|
| Feed Tube diameter | | Balloon diameters, inches | | Test | | | | Cal Vol, |
| Fr | inch | Equatorial | Polar | Vol, ml | a, cm | b, cm | b/a | ml |
| 10 | 0.131 | 0.78 | 0.388 | 3 | 0.991 | 0.493 | 0.497 | 2.026 |
| 12 | 0.157 | 0.834 | 0.416 | 3 | 1.059 | 0.528 | 0.499 | 2.483 |
| 14 | 0.184 | 0.886 | 0.443 | 5 | 1.125 | 0.563 | 0.500 | 2.985 |
| 16 | 0.21 | 0.938 | 0.467 | 5 | 1.191 | 0.593 | 0.498 | 3.527 |
| 18 | 0.236 | 0.99 | 0.48 | 5 | 1.257 | 0.610 | 0.485 | 4.038 |
| 20 | 0.262 | 1.048 | 0.529 | 6 | 1.331 | 0.672 | 0.505 | 4.987 |
| 24 | 0.315 | 1.165 | 0.524 | 6 | 1.480 | 0.665 | 0.450 | 6.104 |

Table 6 compares values of polar and equatorial diameters for a balloon typical of the invention to a conventional balloon when both types of balloons are inflated to approximately the same fill volumes. The fill volumes for Sample D are suitable as predetermined fill volumes. The diameter values of Table 6 are averages of five measurements respectively made using a caliper that is capable of discerning 0.0001 inch increments; the caliper measured the distance without the application of any significant compressive forces on the balloons. For Sample D at each fill volume the polar diameter dimensions that are less than 60% of the equatorial diameters. In comparison, Sample M, a MIC-KEY® 16 Fr low-profile gastronomy feed tube from Kimberly-Clark Corporation, shows the polar and equatorial diameters to be similar for all its corresponding fill volumes. Of note was the inability of the balloon of Sample D to sustainably stretch to contain a fill volume of 8.8 ml; subsequent handling after filling to this volume caused the balloon wall to burst.

Also presented in Table 6 is a similarly measured and averaged value for the diameter of an angioplasty balloon of Sample A. This balloon is in the shape of a cylinder, not a spheroid. The length of this balloon is approximately 2.5 inches; the relatively small diameter and the long length of such balloons make them unsuitable for use as retention components for enteral feed tubes.

TABLE 6

| Sample | Type | Fill Volume, ml | Diameter, inches: Polar | Diameter, inches: Equatorial (E0) | Polar/Eq Ratio |
|---|---|---|---|---|---|
| D | Invention | 4.8 | 0.534 ± 3.8% | 0.948 ± 0.9% | 0.564 |
| | | 6.9 | 0.580 ± 7.3% | 1.047 ± 0.6% | 0.554 |
| | | 8.8 | Burst | Burst | — |
| M | Conventional | 4.8 | 0.853 ± 0.7% | 0.824 ± 0.3% | 1.0362 |
| | | 6.8 | 0.908 ± 0.2% | 0.920 ± 0.3% | 0.987 |
| | | 8.8 | 0.954 ± 0.6% | 1.003 ± 0.2% | 0.952 |
| A | Angioplasty | 4 | — | 0.364 ± 0.9% | — |

Figure 12:
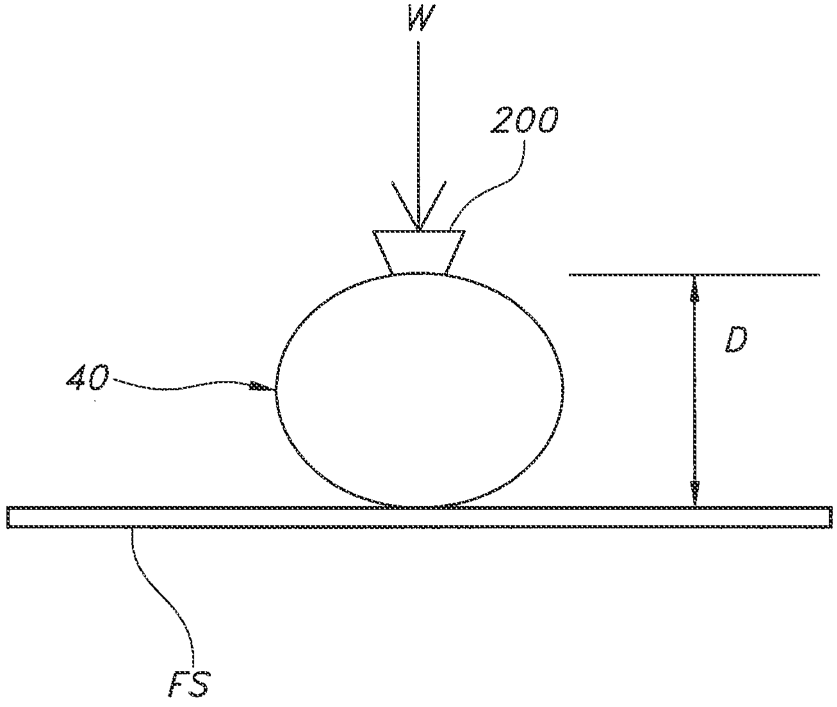
FIG. 12 is a side view illustrating test equipment used to measure stability of a balloon portion of an exemplary inflatable retention device.

The balloons of the invention display relatively stable dimensions above their reserve volumes and definitely at and above their predetermined fill volumes. They are dimensionally stable at these conditions in the sense that they resist distortion in the directions of their polar and equatorial diameters compared to conventional balloons used for enteral feeding devices. Such dimensional stability is illustrated by measuring changes in a given equatorial diameter caused by distorting forces. Such measurements were made by: 1) positioning an inflated balloon of a representative enteral feeding device on a flat hard surface so its polar diameter was essentially parallel to the flat surface and its equatorial diameter was perpendicular to the flat surface and one end of the diameter interfaced with the flat surface, 2) applying a force on the surface of the balloon along the given equatorial diameter at a contact area and at the other end of the equatorial diameter, 3) recording the distance between the flat surface and the contact area. FIG. 12 shows the arrangement of the balloons and other specifics used to make the measurements. Measurements were made on the balloons of Samples D, M, and A.

Referring to FIG. 12, the balloon 40 was placed on a flat surface "FS". The force on the balloon 40 came from various weights "W" (not shown) placed on a circular platen or foot 200 that was 0.6 mm in diameter. The distance "D" was measured by a digital gauge that was connected to the platen 200; this gauge measured 0.00005 inch increments. The weight of the platen and gauge connection contributed to the force; there were no extra, unaccounted force contributions.

The individual dimensional stability measurements for the balloon of Sample D, representing a balloon suitable for the invention, were first made with the balloon inflated to a fill volume of 4.8 ml water at room temperature. Once filled and positioned between the flat surface and the platen, distorting forces (Wgt) were applied to the balloon as shown in FIG. 12 and the distance between the platen and the flat surface measured. The distances were measured with increases in force, decreases in force, and combinations of both. These distances, made along a given equatorial diameter E1, are listed in Table 7 where: the "rep1+" indicates the first sequence of measurements made using increases in weight force; "rep2−" indicates the second sequence of measurements using decreases in weight force; and so forth. The average of the individual distance measurements are calculated in the D4.8 Avg column of Table 7.

TABLE 7

| Sample D with balloon at 4.8 ml fill volume | | | | | | | |
|---|---|---|---|---|---|---|---|
| | Distance, inches | | | | | | % Distor- |
| WGT, gm | E1 rep1+, | E1 rep2− | E1 rep3+ | E1 rep4+ | E1 rep 5− | D4.8 Avg | tion in Diameter |
| 50 | 0.930 | | 0.911 | 0.923 | 0.893 | 0.914 | 3.534 |
| 75 | 0.911 | | | | | 0.911 | 3.852 |
| 100 | 0.900 | 0.888 | 0.889 | 0.897 | | 0.894 | 5.699 |
| 125 | 0.888 | | | | | 0.888 | 6.280 |
| 150 | 0.877 | 0.867 | | 0.874 | | 0.873 | 7.898 |
| 175 | — | — | — | — | — | — | — |
| 200 | 0.857 | 0.846 | 0.845 | 0.853 | | 0.850 | 10.270 |
| 225 | 0.848 | 0.841 | | | | 0.844 | 10.897 |
| 250 | 0.838 | 0.829 | | 0.828 | 0.807 | 0.831 | 12.902 |
| 275 | — | — | — | — | — | — | — |
| 300 | 0.818 | 0.812 | 0.812 | 0.810 | 0.800 | 0.813 | 14.491 |
| 325 | 0.802 | 0.804 | 0.801 | 0.800 | | 0.802 | 15.396 |

To determine the relative dimensional stability, e.g. its distortion in its equatorial diameter, at this fill volume, each D4.8 Avg distance was compared to the E0 value at the matching fill volume from Table F and transformed into a % Distortion in Diameter value. This transformation is calculated for each weight force by: 1) determining the distance difference from the matching E0, 2) dividing by the matching E0 value, 3) expressing the resultant value as percent, by example, Table 7's Eq4.8 avg measurement at 50 gm (0.914013) transforms using Table 7's E0 value at 4.8 fill volume (0.9475) via: 100*(0.9475-0.914013)/0.9475 to yield 3.534301%. Similar measurements, E2, for the balloon of Sample D at 6.9 ml fill volume were made and are listed in Table 8.

TABLE 8

| Sample D with balloon at 6.9 ml fill volume | | | | | | | |
|---|---|---|---|---|---|---|---|
| | Distance, inches | | | | | | % Distor- |
| WGT, gm | E2 rep1+, | E2 rep2− | E2 rep3+ | E2 rep4+ | E2 rep5− | DAvg6.9 | tion in Diameter |
| 50 | 1.042 | 1.018 | 1.020 | 0.995 | 1.018 | 1.018 | 2.709 |
| 75 | 1.032 | 1.007 | 1.009 | | | 1.016 | 2.982 |
| 100 | 1.023 | 0.998 | 1.003 | | | 1.008 | 3.722 |
| 125 | 1.011 | 0.987 | 0.997 | | | 0.998 | 4.678 |
| 150 | 1.002 | 0.977 | 0.989 | | | 0.989 | 5.502 |
| 175 | 0.994 | 0.968 | 0.979 | | | 0.980 | 6.381 |
| 200 | 0.988 | 0.959 | 0.967 | | | 0.971 | 7.249 |
| 225 | 0.979 | 0.951 | 0.962 | | | 0.964 | 7.918 |
| 250 | 0.969 | 0.942 | 0.954 | | | 0.955 | 8.793 |
| 275 | 0.958 | 0.933 | 0.947 | | | 0.946 | 9.653 |
| 300 | 0.953 | 0.930 | 0.940 | | | 0.941 | 10.147 |
| 325 | 0.945 | 0.921 | 0.928 | | | 0.931 | 11.070 |

Similar measurements were made for Sample M, a device with a conventional silicone, at balloon fill volumes of 4.8, 6.8 and 8.8 ml of water. Their measurements, E3, E4, E5, and their respective calculations for averaging (M4.8 Avg, M6.8 Avg, M8.8 Avg) and transformations into Percent (%) Distortion are given in Tables 9 through 11 below.

TABLE 9

| Sample M with balloon at 4.8 ml fill volume | | | | | | | | |
|---|---|---|---|---|---|---|---|---|
| | Distance, inches | | | | | | | % Distor- |
| WGT, gm | E3 rep1+ | E3 rep2− | E3 rep3+ | E3 rep4+ | E3 rep5− | E3 rep6+ | M4.8 Avg | tion in Diameter |
| 50 | 0.777 | 0.730 | 0.773 | 0.774 | 0.723 | 0.769 | 0.758 | 8.010 |
| 75 | | | 0.740 | 0.745 | | | 0.742 | 9.866 |

TABLE 9-continued

| Sample M with balloon at 4.8 ml fill volume | | | | | | | | |
|---|---|---|---|---|---|---|---|---|
| | Distance, inches | | | | | | | % Distortion in Diameter |
| WGT, gm | E3 rep1+ | E3 rep2− | E3 rep3+ | E3 rep4+ | E3 rep5− | E3 rep6+ | M4.8 Avg | |
| 100 | 0.726 | 0.713 | 0.718 | 0.717 | | | 0.718 | 12.773 |
| 125 | 0.714 | | 0.693 | 0.697 | | | 0.701 | 14.865 |
| 150 | | | 0.682 | 0.673 | | | 0.678 | 17.729 |
| 175 | | | | | | | — | — |
| 200 | | | 0.644 | 0.643 | | | 0.644 | 21.858 |
| 225 | | | | | | | — | — |
| 250 | | | 0.613 | 0.605 | 0.580 | | 0.599 | 27.241 |
| 275 | | | | | | | — | — |
| 300 | | | 0.586 | 0.577 | 0.562 | | 0.575 | 30.176 |
| 325 | | | 0.562 | 0.562 | | | 0.562 | 31.755 |

TABLE 10

| Sample M with balloon at 6.8 ml fill volume | | | | |
|---|---|---|---|---|
| | Distance, inches | | | |
| WGT, gm | E4 rep1+, | E4 rep2− | M6.8 Avg | % Distortion in Diameter |
| 50 | 0.872 | 0.865 | 0.868 | 5.680 |
| 75 | 0.848 | 0.844 | 0.846 | 8.056 |
| 100 | 0.836 | 0.810 | 0.823 | 10.582 |
| 125 | 0.817 | 0.805 | 0.811 | 11.873 |
| 150 | 0.790 | 0.784 | 0.787 | 14.507 |
| 175 | 0.775 | 0.775 | 0.775 | 15.825 |
| 200 | 0.769 | 0.759 | 0.764 | 17.020 |
| 225 | 0.749 | 0.747 | 0.748 | 18.731 |
| 250 | 0.732 | 0.730 | 0.731 | 20.605 |
| 275 | 0.722 | 0.715 | 0.718 | 21.950 |
| 300 | 0.704 | 0.701 | 0.703 | 23.674 |
| 325 | 0.690 | 0.685 | 0.687 | 25.345 |

TABLE 11

| Sample M with balloon at 8.8 ml fill volume | | | | |
|---|---|---|---|---|
| | Distance, inches | | | |
| WGT, gm | E5 rep1+, | E5 rep2− | M8.8 Avg | % Distortion in Diameter |
| 50 | 0.968 | 0.946 | 0.957 | 4.567 |
| 75 | 0.933 | | 0.933 | 6.985 |
| 100 | 0.922 | 0.915 | 0.918 | 8.456 |
| 125 | 0.901 | | 0.901 | 10.201 |
| 150 | 0.888 | 0.882 | 0.885 | 11.785 |
| 175 | 0.872 | | 0.872 | 13.093 |
| 200 | 0.854 | 0.851 | 0.852 | 15.013 |
| 225 | 0.842 | | 0.842 | 16.010 |
| 250 | 0.827 | 0.815 | 0.821 | 18.129 |
| 275 | 0.812 | | 0.812 | 19.027 |
| 300 | 0.799 | 0.794 | 0.797 | 20.547 |
| 325 | 0.782 | | 0.782 | 22.043 |

Additionally, similar measurements were made for the diameter of the Sample A angioplasty device; its diameter measurements are expressed as E6. (Not being a spheroid, this balloon lacks a polar diameter.) Table 12 lists these and the average (A4.0 avg) and % Distortion transformation calculations in the same manner as the immediately preceding Tables.

TABLE 12

| Sample A with balloon at 4 ml fill volume | | | | | |
|---|---|---|---|---|---|
| | Distance, inches | | | | |
| WGT, gm | E6 rep1+ | E6 rep2− | E6 rep3+ | A4.0 Avg | % Distortion in Diameter |
| 50 | 0.361 | 0.357 | 0.357 | 0.358 | 1.503 |
| 75 | 0.361 | | | 0.361 | 0.770 |
| 100 | 0.358 | | | 0.358 | 1.594 |
| 125 | 0.355 | | | 0.355 | 2.419 |
| 150 | 0.352 | | | 0.352 | 3.244 |
| 175 | — | — | — | — | — |
| 200 | 0.346 | | | 0.346 | 5.030 |
| 225 | — | — | — | — | — |
| 250 | 0.341 | 0.332 | | 0.337 | 7.470 |
| 275 | — | — | — | — | — |
| 300 | 0.334 | | | 0.334 | 8.329 |
| 325 | 0.326 | | | 0.326 | 10.322 |

Figure 13:
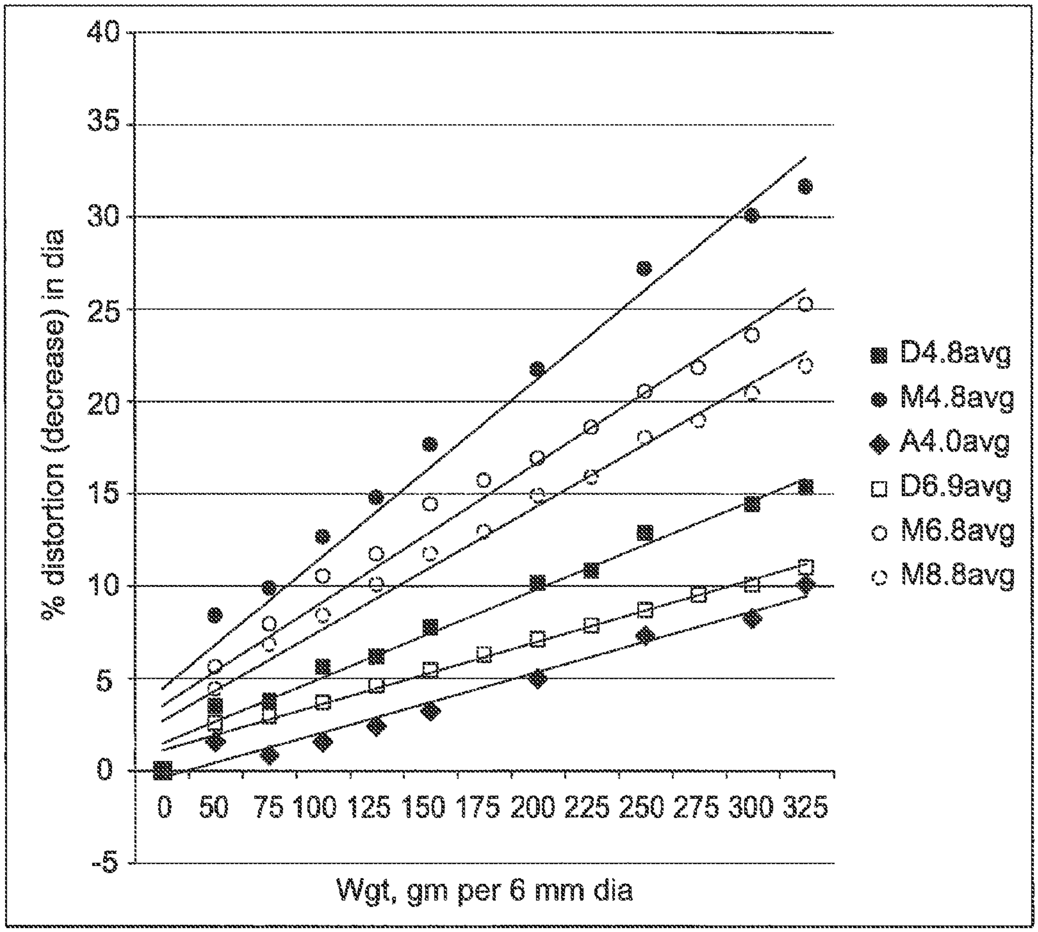
FIG. 13 is an illustration of a graph of data and information from Tables 7 through 12.

FIG. 13 compares the % Distortion in Diameter values of Tables 7-12 with respect to the weight forces (Wgt, gm per 6 mm dia). Linear trend lines are added to help distinguish each fill volume condition from each other.

Another advantage of the invention is minimal impact of the contribution of the balloon to the effective outside diameter of the feed tube between the attachment locations of the balloon. Due to its thin wall, the completely deflated balloon folds and wraps around the feeding tube with negligible thickness contributions. Table 13 illustrates the effects that deflated balloons contribute to effective outside diameters for balloon catheters per measurements made on Samples D, M, and A. Each sample had five measurements made using calipers capable of discerning 0.0001 inch increments in regions without any attached balloons and in regions of attached and completely deflated balloons. The measurements of the feed tubes without attached balloons were averaged to give the Catheter Diameter (C) values in Table 13; those measurements of the feed tubes between balloon attachment locations with completely deflated balloons were averaged to give the Catheter Diameter+Balloon (C+B) values. The ratios of C+B/C in Table 13 clearly show that the balloons suitable for the invention have less impact on the effective outside feed tube diameter than conventional catheters with balloons.

TABLE 13

Effective outside diameters for balloon catheters

| Sample | Catheter Diameter (C), inches | Catheter Diameter + Balloon (C + B), inches | C + B/C |
|---|---|---|---|
| D | 0.214 | 0.206 | 0.962 |
| M | 0.210 | 0.241 | 1.151 |
| A | 0.0625 | 0.086 | 1.378 |

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description. The figures are not drawn to scale and related elements may be omitted so as to emphasize the novel features of the invention. Structural and functional details depicted in the figures are provided for the purpose of teaching the practice of the invention to those skilled in the art and are not intended to be considered limitations. Directional terms such as left, right, front or rear are provided to assist in the understanding of the invention and are not intended to be considered as limitations.

While particular embodiments of the present invention have been described herein; it will be apparent to those skilled in the art that alterations and modifications may be made to the described embodiments without departing from the scope of the appended claims.

We claim:

1. An inflatable retention system for an enteral feeding tube having a base deployed outside the human body and an indwelling retainer which is deployed within a lumen of the body by insertion through a stoma from outside the body, the retention system comprising:

a tube having a proximal end, a distal end, an external tube diameter, and tube walls defining a feeding lumen and an inflation lumen; and an inflatable balloon located at a distal end of the tube in fluid communication with the inflation lumen, the balloon having thin, flexible walls, a predetermined spheroid shape, a reserve volume having a lower limit that is greater than 0.5 milliliters of a fluid and an upper limit at a transition between a non-distended state and a distended state of the balloon in which a fluid in the balloon is under no pressure, and a predetermined fill volume about 1.01 to about 1.5 times greater than an upper limit of the reserve volume, such that upon inflation with a fluid to pressurize fluid in the balloon, the balloon assumes a stable spheroid shape and exhibits a substantially linear pressure versus volume curve to at least the predetermined fill volume.

2. The inflatable retention system of claim 1, wherein the balloon has a collapsed, non-inflated state such that the tube and the thin, flexible walls of the balloon can pass through an orifice having a diameter not more than about 20 percent greater than the external diameter of the tube.

3. The inflatable retention system of claim 1, wherein the substantially linear pressure versus volume curve corresponds to a fluid pressure in the balloon between 2 to about 9 pounds per square inch (14 to 64 kilopascals).

4. The inflatable retention system of claim 3, wherein the balloon has volumes from about 2 milliliters to about 6 milliliters.

5. The inflatable retention system of claim 1, wherein the wall of the balloon has a thickness of from about 5 micrometers to about 100 micrometers.

6. The inflatable retention system of claim 1, wherein the spheroid shape is an oblate spheroid shape.

7. The inflatable retention system of claim 1, wherein the tube has an external tube diameter of from about 3 mm to about 9 mm and the balloon has a diameter of from about 15 mm to about 30 mm at a major axis of the spheroid when under pressure and wherein the ratio of the said balloon diameter to the external tube diameter is greater than three.

8. The inflatable retention system of claim 1, wherein the tube is formed of a material having an elongation of less than about 100 percent at a load of 300 pounds per square inch.

9. The retention system of claim 1 further comprising:

a base located at the proximal end of the tube, the base defining an opening to the feeding lumen, the base having a first end and a second end;

an inflation valve located on the base, the inflation valve in fluid communication with the balloon through the inflation lumen; and an indicator located on the base in fluid communication with the balloon, the indicator configured to provide a discrete visual signal that the volume of the balloon is different from a predetermined fill volume or from a reserve volume.

10. An inflatable retention system for an enteral feeding tube having a base deployed outside the human body and an indwelling retainer which is deployed within a lumen of the body by insertion through a stoma from outside the body, the retention system comprising:

a tube having a proximal end, a distal end, an external tube diameter, and tube walls defining a feeding lumen and an inflation lumen; and an inflatable balloon located at a distal end of the tube in fluid communication with the inflation lumen, the balloon having thin, flexible walls, each wall ranging from about 5 micrometers to about 100 micrometers in thickness, and a collapsed, non-inflated state such that the tube and the thin, flexible walls of the balloon can pass through an orifice having a diameter not more than about 20 percent greater than the external diameter of the tube, a predetermined spheroid shape, a reserve volume having a lower limit that is greater than 0.5 milliliters of a fluid and an upper limit at a transition between a non-distended state and a distended state of the balloon in which a fluid in the balloon is under no pressure, and a predetermined fill volume about 1.01 to about 1.5 times greater than an upper limit of the reserve volume, such that upon inflation with a fluid to pressurize fluid in the balloon, the balloon assumes a stable spheroid shape and exhibits a substantially linear pressure versus volume curve to at least the predetermined fill volume.

* * * * *